United States Patent
Garnero et al.

(10) Patent No.: US 9,115,190 B2
(45) Date of Patent: Aug. 25, 2015

(54) SEQUENCES, ANTIBODIES, METHODS AND KITS FOR DETECTION AND IN VITRO ASSAY OF PERIOSTIN, IN ORDER TO PROVIDE A DIAGNOSIS, FOLLOW-UP OR PROGNOSIS OF DISEASES AND BIOLOGICAL PHENOMENA INVOLVING PERIOSTIN

(75) Inventors: Patrick Garnero, Gaujac (FR); Sylvain Contie, Aix-en-Provence (FR); Nathalie Rousselot, Les Cotes d'Arey (FR); Philippe Clezardin, Lyons (FR)

(73) Assignees: SYNARC SAS, Lyons (FR); INSERM, Paris (FR)

( * ) Notice: Subject to any disclaimer, the term of this patent is extended or adjusted under 35 U.S.C. 154(b) by 641 days.

(21) Appl. No.: 13/375,870

(22) PCT Filed: Jun. 3, 2010

(86) PCT No.: PCT/EP2010/057795
§ 371 (c)(1),
(2), (4) Date: Jan. 20, 2012

(87) PCT Pub. No.: WO2010/139768
PCT Pub. Date: Dec. 9, 2010

(65) Prior Publication Data
US 2012/0219977 A1 Aug. 30, 2012

(30) Foreign Application Priority Data
Jun. 3, 2009 (FR) .................................. 09 53646

(51) Int. Cl.
| | | |
|---|---|---|
| G01N 31/00 | (2006.01) |
| G01N 33/53 | (2006.01) |
| C07K 16/18 | (2006.01) |
| C07K 14/475 | (2006.01) |
| C07K 16/22 | (2006.01) |
| G01N 33/574 | (2006.01) |
| G01N 33/68 | (2006.01) |

(52) U.S. Cl.
CPC .............. *C07K 16/18* (2013.01); *C07K 14/475* (2013.01); *C07K 16/22* (2013.01); *G01N 33/57415* (2013.01); *G01N 33/689* (2013.01); *G01N 33/6887* (2013.01); *G01N 2333/705* (2013.01); *G01N 2800/00* (2013.01); *G01N 2800/108* (2013.01); *G01N 2800/56* (2013.01)

(58) Field of Classification Search
CPC ... A61K 31/713; A61K 45/06; C07D 487/04; C12N 15/113
USPC ......................................................... 422/430
See application file for complete search history.

(56) References Cited

U.S. PATENT DOCUMENTS

| 2007/0167369 A1 | 7/2007 | Nam et al. ...................... 514/12 |
| 2008/0274955 A1 | 11/2008 | Nam et al. ...................... 514/12 |

FOREIGN PATENT DOCUMENTS

| WO | WO 01/57062 | 8/2001 | |
| WO | WO 03/016471 | 2/2003 | |
| WO | WO03016471 A2 * | 2/2003 | ............. C07K 14/47 |
| WO | WO 2005/099743 | 10/2005 | |
| WO | WO2007096142 A2 * | 8/2007 | ........... G01N 33/574 |

OTHER PUBLICATIONS

Contie et al., "Development of a new ELISA for serum periostin: Growth-related changes and effects of bisphosphonate," 44 *Bone Suppl. S,* S270 (2009) & 36th European Symposium on Calcified Tissues (Vienna, Austria; May 23-27, 2009).
Litvin et al., "Expression and Function of Periostin-Isoforms in Bone", 92 *J. Cellular Biochem.* 1044 (2004).
Sasaki et al., "Novel chemiluminescence assay for the serum periostin levels in woman with preclampsia and in mormotensive pregnant woman", 186 *Am. J. Obstetrics & Gynecology* 103 (2002).
Yoshioka et al., "Suppression of Anchorage-Independent Growth of Human Cancer Cell Lines by the TRIF52/Periostin/OSF-2 Gene," 279 *Experimental Cell Research* 91 (2002).
Horiuchi et al., "Identification and Characterization of a Novel Protein, Periostin, with Restricted Expression to Periosteum and Periodontal Ligament and Increased Expression by Transforming Growth Factor β," 14 *J. Bone & Mineral Research* 1239 (1999).
Takeshita et al., "Osteoblast-specific factor 2: cloning of a putative bone adhesion protein with homology with the insect protein fasciclin I," 294 *Biochem. J.* 271 (1993).
Coutu et al., "Periostin, a Member of a Novel Family of Vitamin K-dependent Proteins, Is Expressed by Mesenchymal Stromal Cells," 283 *J. Biological Chem.* 17991 (2008).

* cited by examiner

*Primary Examiner* — Lisa Cook
(74) *Attorney, Agent, or Firm* — James C. Lydon

(57) ABSTRACT

Detection sequences of periostin having from 6 to 30 amino acids and which include all or part of peptide sequence SEQ ID No. 1, SEQ ID No. 2 or SEQ ID No. 3, or a homologous peptide sequence. Antibodies suitable for specifically recognizing minimally one of these detection sequences, including an anti-periostin antibody, are disclosed. Periostin detection and dosage processes and kits that use these antibodies are also disclosed. A periostin marker for early diagnosis, tracking and prognosis of pathologies that involve periostin, including benign osteolysis such as inflammatory diseases, including osteoarticular diseases, and malignant osteolysis, such as cancers with bone metastases, is provided.

6 Claims, 13 Drawing Sheets

Figure 1

SEQ ID N°1 Homo sapiens/Mus musculus

KGFEPGVTNILKTTQGSK

SEQ ID N°2 Homo sapiens

ETLEGNTIEIGCDGDSI

SEQ ID N°3 Mus musculus

EAITGGAVGEAITGGAV

Figure 2A

SEQ ID N°4 Périostine Homo sapiens 836 acides aminés ; peptide signal 1- 21

```
MIPFLPMFSL LLLLIVNPIN ANNHYDKILA HSRIRGRDQG PNVCALQQIL GTKKKYFSTC
KNWYKKSICG
QKTTVLYECC PGYMRMEGMK GCPAVLPIDH VYGTLGIVGA TTTQRYSDAS KLREEIEGKG
SFTYFAPSNE
AWDNLDSDIR RGLESNVNVE LLNALHSHMI NKRMLTKDLK NGMIIPSMYN NLGLFINHYP
NGVVTVNCAR
IIHGNQIATN GVVHVIDRVL TQIGTSIQDF IEAEDDLSSF RAAAITSDIL EALGRDGHFT
LFAPTNEAFE
KLPRGVLERF MGDKVASEAL MKYHILNTLQ CSESIMGGAV FETLEGNTIE IGCDGDSITV
NGIKMVNKKD
IVTNNGVIHL IDQVLIPDSA KQVIELAGKQ QTTFTDLVAQ LGLASALRPD GEYTLLAPVN
NAFSDDTLSM
VQRLLKLILQ NHILKVKVGL NELYNGQILE TIGGKQLRVF VYRTAVCIEN SCMEKGSKQG
RNGAIHIFRE
IIKPAEKSLH EKLKQDKRFS TFLSLLEAAD LKELLTQPGD WTLFVPTNDA FKGMTSEEKE
ILIRDKNALQ
NIILYHLTPG VFIGKGFEPG VTNILKTTQG SKIFLKEVND TLLVNELKSK ESDIMTTNGV
IHVVDKLLYP
ADTPVGNDQL LEILNKLIKY IQIKFVRGST FKEIPVTVYT TKIITKVVEP KIKVIEGSLQ
PIIKTEGPTL
TKVKIEGEPE FRLIKEGETI TEVIHGEPII KKYTKIIDGV PVEITEKETR EERIITGPEI
KYTRISTGGG
ETEETLKKLL QEEVTKVTKF IEGGDGHLFE DEEIKRLLQG DTPVRKLQAN KKVQGSRRRL REGRSQ
```

Figure 2B

SEQ ID N°5 Périostine Mus musculus 838 acides aminés, peptide signal 1- 21

```
MVPLLPLYAL LLLFLCDINP ANANSYYDKV LAHSRIRGRD QGPNVCALQQ ILGTKKKYFS
SCKNWYQGAI
CGKKTTVLYE CCPGYMRMEG MKGCPAVMPI DHVYGTLGIV GATTTQHYSD VSKLREEIEG
KGSYTYFAPS
NEAWENLDSD IRRGLENNVN VELLNALHSH MVNKRMLTKD LKHGMVIPSM YNNLGLFINH
YPNGVVTVNC
ARVIHGNQIA TNGVVHVIDR VLTQIGTSIQ DFLEAEDDLS SFRAAAITSD LLESLGRDGH
FTLFAPTNEA
FEKLPRGVLE RIMGDKVASE ALMKYHILNT LQCSEAITGG AVFETMEGNT IEIGCEGDSI
SINGIKMVNK
KDIVTKNGVI HLIDEVLIPD SAKQVIELAG KQQTTFTDLV AQLGLASSLK PDGEYTLLAP
VNNAFSDDTL
SMDQRLLKLI LQNHILKVKV GLSDLYNGQI LETIGGKQLR VFVYRTAICI ENSCMVRGSK
QGRNGAIHIF
REIIQPAEKS LHDKLRQDKR FSIFLSLLEA ADLKDLLTQP GDWTLFAPTN DAFKGMTSEE
RELLIGDKNA
LQNIILYHLT PGVYIGKGFE PGVTNILKTT QGSKIYLKGV NETLLVNELK SKESDIMTTN
GVIHVVDKLL
YPADIPVGND QLLELLNKLI KYIQIKFVRG STFKEIPMTV YTTKIITKVV EPKIKVIQGS
LQPIIKTEGP
AMTKIQIEGD PDFRLIKEGE TVTEVIHGEP VIKKYTKIID GVPVEITEKQ TREERIITGP
EIKYTRISTG
GGETGETLQK FLQKEVSKVT KFIEGGDGHL FEDEEIKRLL QGDTPAKKIP ANKRVQGPRR RSREGRSQ
```

SEQ ID N°6: XP_001512245
PREDICTED: similar to periostin, osteoblast specific factor [Ornithorhynchus anatinus]
gi|149635842|ref|XP_001512245.1|[149635842]

Figure 2C

SEQ ID N°7: XP_001085920
PREDICTED: periostin, osteoblast specific factor isoform 4 [Macaca mulatta]
gi|109120498|ref|XP_001085920.1|[109120498]

SEQ ID N°8: XP_001085575
PREDICTED: periostin, osteoblast specific factor isoform 1 [Macaca mulatta]
gi|109120500|ref|XP_001085575.1|[109120500]

SEQ ID N°9: XP_001085814
PREDICTED: periostin, osteoblast specific factor isoform 3 [Macaca mulatta]
gi|109120502|ref|XP_001085814.1|[109120502]

SEQ ID N°10: XP_001085700
PREDICTED: periostin, osteoblast specific factor isoform 2 [Macaca mulatta]
gi|109120504|ref|XP_001085700.1|[109120504]

SEQ ID N°11: XP_001148441
PREDICTED: periostin, osteoblast specific factor isoform 10 [Pan troglodytes]
gi|114649406|ref|XP_001148441.1|[114649406]

SEQ ID N°12: XP_001148156
PREDICTED: periostin, osteoblast specific factor isoform 6 [Pan troglodytes]
gi|114649408|ref|XP_001148156.1|[114649408]

SEQ ID N°13: XP_001148083
PREDICTED: periostin, osteoblast specific factor isoform 5 [Pan troglodytes]
gi|114649410|ref|XP_001148083.1|[114649410]

SEQ ID N°14: XP_001148381
PREDICTED: periostin, osteoblast specific factor isoform 9 [Pan troglodytes]
gi|114649412|ref|XP_001148381.1|[114649412]

SEQ ID N°15: XP_001148299
PREDICTED: periostin, osteoblast specific factor isoform 8 [Pan troglodytes]
gi|114649415|ref|XP_001148299.1|[114649415]

Figure 2D

SEQ ID N°16: XP_001148230
PREDICTED: periostin, osteoblast specific factor isoform 7 [Pan troglodytes]
gi|114649417|ref|XP_001148230.1|[114649417]

SEQ ID N°17: XP_001148006
PREDICTED: periostin, osteoblast specific factor isoform 4 [Pan troglodytes]
gi|114649419|ref|XP_001148006.1|[114649419]

SEQ ID N°18: XP_001147936
PREDICTED: periostin, osteoblast specific factor isoform 3 [Pan troglodytes]
gi|114649421|ref|XP_001147936.1|[114649421]

SEQ ID N°19: XP_001147873
PREDICTED: periostin, osteoblast specific factor isoform 2 [Pan troglodytes]
gi|114649423|ref|XP_001147873.1|[114649423]

SEQ ID N°20: XP_509634
PREDICTED: periostin, osteoblast specific factor isoform 11 [Pan troglodytes]
gi|114649425|ref|XP_509634.2|[114649425]

SEQ ID N°21: XP_001147730
PREDICTED: periostin, osteoblast specific factor isoform 1 [Pan troglodytes]
gi|114649427|ref|XP_001147730.1|[114649427]

SEQ ID N°22: BAA02836
osteoblast specific factor 2 [Homo sapiens]
gi|393319|dbj|BAA02836.1|[393319]

SEQ ID N°23: NP_006466
periostin, osteoblast specific factor [Homo sapiens]
gi|5453834|ref|NP_006466.1|[5453834]

SEQ ID N°24: AAN17733
extracellular matrix protein periostin-bm [Homo sapiens]
gi|23345100|gb|AAN17733.1|[23345100]

Figure 2E

SEQ ID N°25: CAH70104
periostin, osteoblast specific factor [Homo sapiens]
gi|55661654|emb|CAH70104.1|[55661654]

SEQ ID N°26: CAH70105
periostin, osteoblast specific factor [Homo sapiens]
gi|55661655|emb|CAH70105.1|[55661655]

SEQ ID N°27: CAH70106
periostin, osteoblast specific factor [Homo sapiens]
gi|55661656|emb|CAH70106.1|[55661656]

SEQ ID N°28: AAY15840
periodontal ligament-specific periostin [Homo sapiens]
gi|62824474|gb|AAY15840.1|[62824474]

SEQ ID N°29: Q15063
Periostin precursor (PN) (Osteoblast-specific factor 2) (OSF-2)
gi|93138709|sp|Q15063.2|POSTN_HUMAN[93138709]

SEQ ID N°30: EAX08592
periostin, osteoblast specific factor, isoform CRA_b [Homo sapiens]
gi|119628997|gb|EAX08592.1|[119628997]

SEQ ID N°31: XP_534490
PREDICTED: similar to Periostin precursor (PN) (Osteoblast-specific factor 2) (OSF-2) isoform 1 [Canis familiaris]
gi|73993197|ref|XP_534490.2|[73993197]

SEQ ID N°32: XP_856272
PREDICTED: similar to Periostin precursor (PN) (Osteoblast-specific factor 2) (OSF-2) isoform 2 [Canis familiaris]
gi|73993199|ref|XP_856272.1|[73993199]

Figure 2F

SEQ ID N°33: XP_856313
PREDICTED: similar to Periostin precursor (PN) (Osteoblast-specific factor 2) (OSF-2) isoform 3 [Canis familiaris]
gi|73993201|ref|XP_856313.1|[73993201]

SEQ ID N°34: XP_856355
PREDICTED: similar to osteoblast specific factor 2 (fasciclin I-like) isoform 4 [Canis familiaris]
gi|73993203|ref|XP_856355.1|[73993203]

SEQ ID N°35: XP_001495882
PREDICTED: similar to periostin, osteoblast specific factor isoform 2 [Equus caballus]
gi|149730161|ref|XP_001495882.1|[149730161]

SEQ ID N°36: XP_001495899
PREDICTED: similar to periostin, osteoblast specific factor isoform 3 [Equus caballus]
gi|149730163|ref|XP_001495899.1|[149730163]

SEQ ID N°37: XP_001495863
PREDICTED: similar to periostin, osteoblast specific factor isoform 1 [Equus caballus]
gi|149730165|ref|XP_001495863.1|[149730165]

SEQ ID N°38: XP_001495934
PREDICTED: similar to periostin, osteoblast specific factor isoform 4 [Equus caballus]
gi|149730167|ref|XP_001495934.1|[149730167]

SEQ ID N°39: NP_001035569
periostin, osteoblast specific factor [Bos taurus]
gi|95147666|ref|NP_001035569.1|[95147666]

SEQ ID N°40: NP_056599
periostin, osteoblast specific factor [Mus musculus]
gi|7657429|ref|NP_056599.1|[7657429]

Figure 2G

SEQ ID N°41: AAH31449
Postn protein [Mus musculus]
gi|21618671|gb|AAH31449.1|[21618671]

SEQ ID N°42: BAC27122
unnamed protein product [Mus musculus]
gi|26326757|dbj|BAC27122.1|[26326757]

SEQ ID N°43: Q62009
Periostin precursor (PN) (Osteoblast-specific factor 2) (OSF-2)
gi|46576895|sp|Q62009.2|POSTN_MOUSE[46576895]

SEQ ID N°44: AAT48882
periostin-like factor protein [Mus musculus]
gi|49036571|gb|AAT48882.1|[49036571]

SEQ ID N°45: BAE32339
unnamed protein product [Mus musculus]
gi|74180343|dbj|BAE32339.1|[74180343]

SEQ ID N°46: EDL35258
periostin, osteoblast specific factor, isoform CRA_b [Mus musculus]
gi|148703311|gb|EDL35258.1|[148703311]

SEQ ID N°47: EDL35259
periostin, osteoblast specific factor, isoform CRA_c [Mus musculus]
gi|148703312|gb|EDL35259.1|[148703312]

SEQ ID N°48: EDL35260
periostin, osteoblast specific factor, isoform CRA_d [Mus musculus]
gi|148703313|gb|EDL35260.1|[148703313]

SEQ ID N°49: EDL35261
periostin, osteoblast specific factor, isoform CRA_e [Mus musculus]
gi|148703314|gb|EDL35261.1|[148703314]

Figure 2H

SEQ ID N°50: EDM14934
periostin, osteoblast specific factor (predicted), isoform CRA_b [Rattus norvegicus]
gi|149064783|gb|EDM14934.1|[149064783]

SEQ ID N°51: EDM14935
periostin, osteoblast specific factor (predicted), isoform CRA_c [Rattus norvegicus]
gi|149064784|gb|EDM14935.1|[149064784]

SEQ ID N°52: EDM14936
periostin, osteoblast specific factor (predicted), isoform CRA_d [Rattus norvegicus]
gi|149064785|gb|EDM14936.1|[149064785]

SEQ ID N°53: EDM14937
periostin, osteoblast specific factor (predicted), isoform CRA_e [Rattus norvegicus]
gi|149064786|gb|EDM14937.1|[149064786]

SEQ ID N°54: NP_001102020
periostin, osteoblast specific factor [Rattus norvegicus]
gi|157823757|ref|NP_001102020.1|[157823757]

Figure 3
A
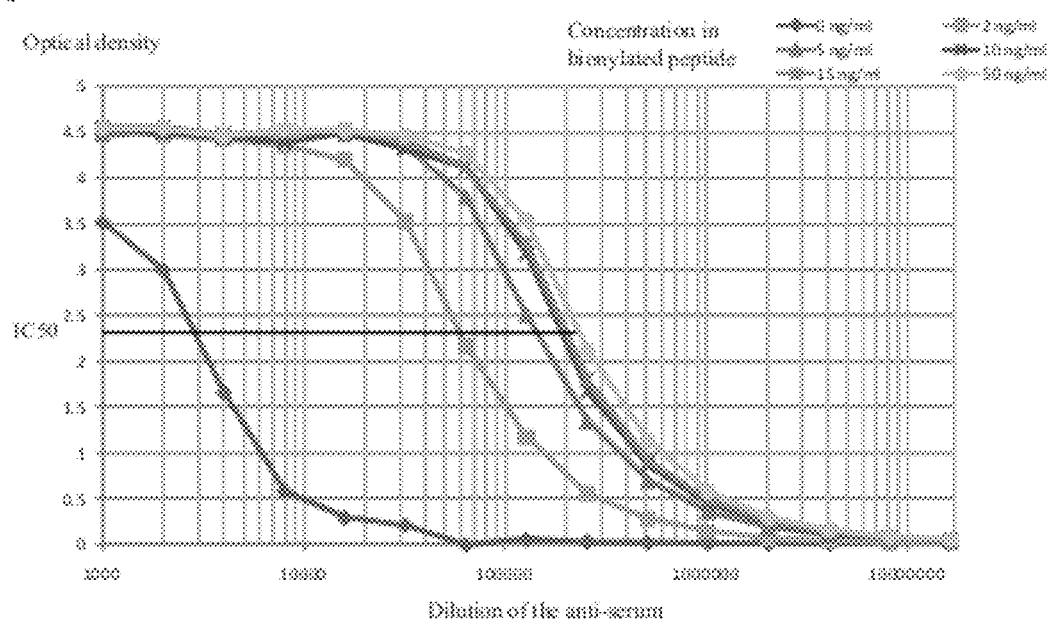
B
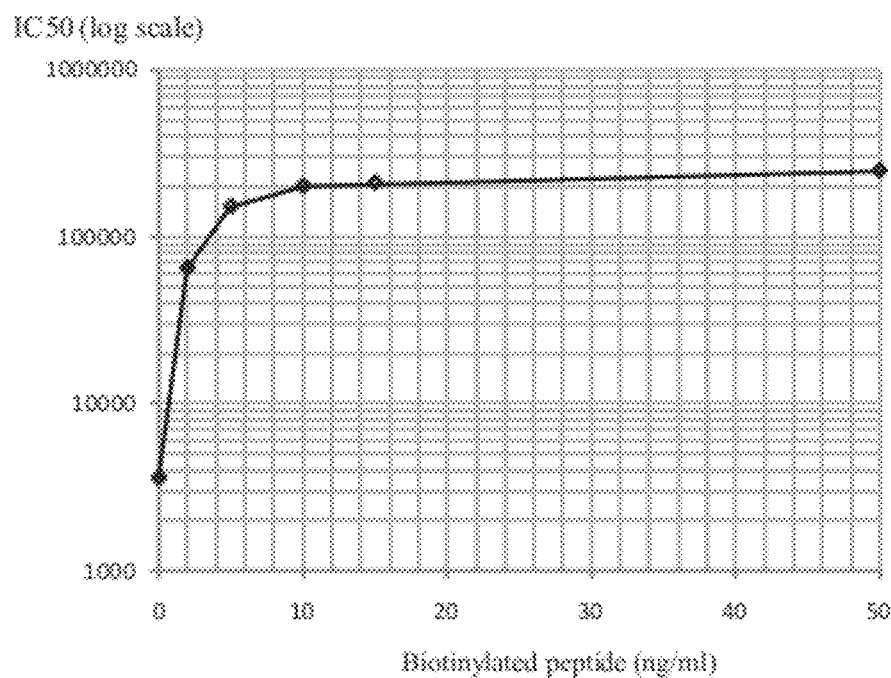

WM: standard of molecular weight
rH: human recombinant periostin
rM: murine recombinant periostin A: mouse in growth stage (age: 3 weeks); B: adult mouse (age: 12 weeks); PO: perioste.

SEQUENCES, ANTIBODIES, METHODS AND KITS FOR DETECTION AND IN VITRO ASSAY OF PERIOSTIN, IN ORDER TO PROVIDE A DIAGNOSIS, FOLLOW-UP OR PROGNOSIS OF DISEASES AND BIOLOGICAL PHENOMENA INVOLVING PERIOSTIN

TECHNICAL SCOPE OF THE INVENTION

The scope of the invention is that of tools and methods for the detection and in vitro dosage of periostin, notably for the diagnosis, tracking (evaluation) and prognosis of pathologies or biological phenomena involving periostin. The pathologies in question it notably involve bone diseases such as osteoporosis, osteoarticular diseases such as arthrosis and rheumatoid polyarthritis, but also certain cancers with strong metastatic powers such as breast cancer and prostate cancer. The non-pathological biological phenomena in question involving periostin can involve the modification or remodeling of the periosteum and joint cartilage, the latter being linked for example to an individual's growth, a change in motor activity or to hormonal changes.

More specifically, the invention targets protein sequences of in vitro periostin detection, the recognition means of these sequences (preferably antibodies), processes for obtaining these recognition means, processes and kits for the detection and dosage implementing these means, in view of applications for the diagnostic-type, tracking and prognosis of the aforementioned diseases, notably bone or osteoarticular diseases and metastatic cancers.

The invention also concerns nucleic sequence coding for protein detection sequences.

PRIOR ART AND TECHNICAL PROBLEM

The skeleton is made up of different types of bones: long bones and short bones, flat bones and intermediate bones. They have essential physiological roles. In effect, in addition to their role of providing a framework and protecting the internal organs, they are important for the formation of blood and immune-defense cells, calcium and mineral metabolism and the growth of the individual. They are also involved in the locomotor system due to the muscles that inserted on them and to the joint system.

The periosteum is the membrane that surrounds the outside of flat bones and long bones near their diaphyses and metaphyses. It has several particularities and functions. In effect, it is the "passage" through which the vascular and nervous systems reach the interior of the bone. It acts as an interface with the extra-bone elements such as tendons and ligaments. It reacts to mechanical stresses (transmitted by ligaments and tendons, tensile stresses, compression stresses) by structural adaptations. Moreover, it is the seat of the peripheral osteogenesis that is crucial for the growth of the external diameter of the long bones and therefore for their solidity. The periosteum's metabolism is regulated by endogen-origin (hormones) or exogen-origin signals (therapeutic agents). The bone is a structure that evolves over the life of an individual. This evolution is linked to a physiological equilibrium (homeostasia) between the activity of two cell types: on one hand, the cells that assure the formation and mineralization of bones (osteoblasts, OBL) and on the other, cells that assure the deterioration of bones (osteoclasts, OCL). Certain pathological or other events can disturb this physiological equilibrium in bones, such as certain cancers or a variation in the estrogen level.

Certain cancers have a strong metastatic power such as breast or prostate cancer. Bone metastases are frequent complications of these cancers. They are responsible at the clinical level for fractures, hypercalcemia and pains that can determine a life-or-death prognosis or quickly deteriorate the quality of life of a patient. These metastases dramatically modify bone homeostasis with primarily an osteolytic impact in breast cancer or an osteoblastic impact in the case of prostate cancer.

One of the major proteins that constitute the periosteum and implied in the metabolism of the bone is periostin. This protein is part of the extracellular bone matrix. It is secreted for the most part by OBL precursors and OBLs, but also by OCLs and has a role in the adhesion, recruitment and differentiation of osteoblastic progenitors (Horiuchi K, Kudo A. Identification and characterization of a novel protein, Periostin, with restricted expression to periosteum and periodontal ligament and increased expression by transforming growth factor β. J Bone Miner Res. 1999;14(7): 1239-1249 and Litvin J, Safadi F F. Expression and function of periostin-isoforms in bone. J Cell Biochem. 2004; 92: 1044-1061). Its expression is activated by various growth factors. Periostin can undergo post-transductional modifications such as for example gamma-carboxylation (Coutu D L, Wu J H, Monette A, Rivard G E, Blostein M D, Galipeau J. Periostin: a member of a novel family of vitamin k-dependent proteins is expressed by mesenchymal stromal cells. J. Biol. Chem. 2008 Apr. 30). This modification entails on one hand a change in 3-dimensional conformation and on the other an increase in affinity of the periostin with regard to the mineral matrix.

Being aware of this protein's involvement in bone metabolism, it's use was envisioned for the diagnosis, prognosis and tracking of bone-related pathologies.

Patent EP-B-1442295 thus discloses a diagnostic method of these pathologies using the fact that the serum rates of periostin are high in the case of breast cancer and pre-eclampsia. This method is based on the use of different isoforms of periostin and antibodies specifically recognizing them. The latter are used to dose in a sample all the isoforms of periostin or a particular isoform by an Enzyme-Linked Immunosorbent Assay (ELISA) sandwich technique. This method, however, is not economical, since it requires the generation of an entire panel of antibodies to dose the total periostin and has shown risks in the reliability of its dosage, since considering the various possible problems of cross reactions and accordingly the lack of specificity. Moreover, although this method does allow for diagnosis, it does not provide for the prognosis or tracking of patients who received a medical and/or surgical treatment for pathologies that involve special isoforms of periostin.

Moreover, periostin has been used in the diagnosis of pathologies other than those related to the bone. Patent application WO-A-2007/077934 describes the preparation of specific antibodies of periostin and their use in a process for detecting this protein for the diagnosis of pathologies such as cardiac pathologies, aneurysm and highly metastatic cancers. To this end, a number of antibodies is actually prepared, each being specific to a special isoform of the periostin. This presents the same economic disadvantages (cost, time, specificity) as the aforementioned patent EP-B-1442295.

Patent application WO-A-2007/096142 describes a method for identifying diseases or conditions associated to a neovascularization in a tissue, by the detection of at least one specific protein of said tissue and by the use of specific antibodies of this (or these) protein(s). One of the proteins used for this purpose is periostin in its precursor form, its isoforms and new protein variants. The diseases targeted are macular degeneration, arthritis, arthrosclerosis and/or tumors, in particular kidney tumors. Thus, this process generates a multitude of antibodies directed against antigens of different protein sequences with the same disadvantages as indicated above.

Patent application WO-A-2005/019471 describes a method to diagnose PLF-related diseases (periostin like factor), a special isoform of periostin. This method is based on the use of an immune-enzymatic test with a specific antibody of this isoform; the epitope recognized by said antibody is in the variable portion of the periostin. This method only makes it possible to dose a special form of periostin and not the total expressed periostin.

PRINCIPAL OBJECTIVES OF THE INVENTION

In view of this prior art, it was therefore desirable to find new means that are specific, simple, reliable, precise and economic for the in vitro determination of the rate of total expressed periostin and the rate of under-carboxylated periostin (totally or partially) and carboxylated periostin directly or indirectly, in order to allow a diagnosis, a tracking, a prognosis and the treatment of pathologies involving periostin and/or to evaluate non-pathological biological phenomena such as the metabolic activity of the bone. Also, the inventors have developed a sequence for detecting total periostin and recognition means of this detection sequence that allows the in vitro dosage of the total periostin, or perhaps the carboxylated periostin and the undercarboxylated periostin, in biological fluids.

Another objective of the invention is to supply means and processes for the detection and dosage of the total periostin, without distinguishing the various isoforms, and the under-carboxylated periostin and indirectly or directly (by specific use of antibodies only recognizing the carboxylated form of the periostin) of the carboxylated periostin, in view of displaying and/or understanding biological phenomena involving periostin, but also in view of improving the early diagnosis, the treatment, the tracking and the prognosis of diseases involving periostin.

Another objective of this invention is to supply economic and high-performing study processes of the biological phenomena involving periostin, and the early diagnosis, tracking, treatment and prognosis of diseases involving periostin.

Another objective of this invention is to provide kits for the detection and dosage of the periostin useful for the aforementioned processes.

BRIEF DESCRIPTION OF THE INVENTION

After extended research and by using sophisticated tools with special selection criteria (exposure, immunogenicity, etc.), the inventors have achieved these objectives by developing a new peptide sequence for the detection of total periostin. These detection means make it possible to detect the total periostin without distinguishing the various isoforms of this protein and independently of the cleavages that frequently occur at the end of the proteins. In fact, by using the modeling, the inventors have been able to isolate in the constant part of the periostin, a restricted and highly exposed peptide sequence. This detection sequence corresponds to a given peptide sequence and its homologs. This detection sequence provides the simple, early, reliable, high-performing, specific and economical detection of the biological phenomena or pathologies involving periostin.

This invention therefore concerns a peptide sequence (PS) for the detection of periostin, characterized in that it includes or is made up of a sequence of 6 to 30 (preferably 15 to 26) amino acids and includes all or part of peptide sequence SEQ ID no. 1, SEQ ID no. 2 or SEQ ID no. 3, or a peptide sequence with a degree of homology greater than or equal to 80%, preferably greater than or equal to 85% with regard to at least one of the sequences: SEQ ID no. 1, SEQ ID no. 2 and SEQ ID no. 3.

The nucleic sequence coding the PS detection sequence forms another object of the invention.

This invention also concerns:

Means for the detection of periostin, including a specific PS recognition tool, made up of at least one anti-periostin antibody and/or at least one of its functional fragments (Ac anti-periostin), specific to SEQ ID no. 1, SEQ ID no. 2, SEQ ID no. 3, or of a peptide sequence with a degree of homology greater than or equal to 80%, preferably greater than or equal to 85% with regard to at least one of the sequences: SEQ ID no. 1, SEQ ID no. 2 and SEQ ID no. 3.

A process for the production of these means for the means for the periostin detection, in particular of Ac [antigen carrier] anti-periostin, characterized in that it essentially consists of:

a. Implementing at least one antigen represented by a peptide sequence (PS) for the periostin detection made up of 6 to 30 amino acids and including all or part of peptide sequence SEQ ID no. 1, SEQ ID no. 2 or SEQ ID no. 3, or a peptide sequence with a degree of homology greater than or equal to 80%, preferably greater than or equal to 85% with regard to at least one of the sequences: SEQ ID no. 1, SEQ ID no. 2 and SEQ ID no. 3, b. Couple said antigen to at least one carrier molecule, c. Recover blood/plasma/serum from an animal which was previously injected with the antigen-carrier molecule pair, d. Select specific PS antibodies by placing the serum/plasma recovered in phase d) with PS antigens, e. Possibly purify the antibodies.

A process of detection and possibly dosage of total periostin in a biological sample, characterized in that it essentially consists of I. Preparing a biological sample, II. Placing said biological sample in the presence of with the aforementioned detection means, III. Show Ac anti-periostin/PS complexes formed;

IV. possibly dose these Ac anti-periostin/PS complexes formed to deduct the concentration in periostin in the sample.

A process for the detection and possibly dosage of under-carboxylated periostin (UCP), to distinguish it from carboxylated periostin (CP), characterized in that it consists essentially of:

$I^{UCP}$.—preparing a biological sample, $I^{UCP}$.1—placing said biological sample in presence in a given medium with a support suitable to fix the CP preferably to the UCP or inversely, said support being:

advantageously a support having an affinity with regard to the CP greater than that with regard to the UCP;

and, even more advantageously, a support including hydroxyapatite;

and even more advantageously, a support including the bone mineral matrix, $I^{UCP}$.2—possibly stir said medium;

$I^{UCP}$.3—once the binding has been performed, separate (preferably by gradient of density, and even more preferably, by centrifugation) the binding support loaded in CP or in UCP (preferably in CP) of the rest of the medium;

$II^{UCP}$. Place in the presence of the binding support loaded in CP or in UCP (preferably in CP) or the rest of the medium with the aforementioned detection means, the latter alternative being preferred;

$III^{UCP}$. isolate any Ac anti-periostin/PS complexes that are formed;

$IV^{UCP}$. dose these Ac anti-periostin/PS complexes that are formed to deduct the concentration in CP periostin in the binding support or in UCP periostin in the rest of the medium, this latter alternative being preferred, and lastly in the sample.

A process of isolating and evaluating a non-pathological biological phenomenon involving periostin, or diagnosis, tracking or prognosis of a pathology involving periostin, or determining the efficacy of a medication adapted to the treatment of a pathology involving periostin, characterized in that it consists of implementing said process for the detection and possibly dosage of total periostin in a biological sample.

A periostin in vitro dosage and detection kit, in a biological sample, characterized in that it includes the aforementioned detection means of periostin, reagents and equipment for the detection, or even the dosage, any Ac anti-periostin/PS complexes formed, according to stage III, or perhaps stage IV, of the aforementioned process for the detection and possibly the dosage of total periostin, and an isolation notice.

A detection and dosage kit of undercarboxylated periostin (UCP), characterized in that it includes the aforementioned detection means of periostin, reagents and equipment for the detection, perhaps even the dosage, of any Ac anti-periostin/PS complexes formed according to stage III, or stage IV, of the aforementioned process of detection and possibly the dosage of total periostin, a medium for the implementation of stages $I^{UCP}$ and $II^{UCP}$ of the aforementioned detection process of detection and possibly of dosage of undercarboxylated periostin (UCP), i.e., a medium capable of binding the CP preferably to the UCP or conversely, with said medium being:

advantageously a medium with an affinity with regard to the CP greater than that with regard to the UCP;

and, more advantageously, a medium including the hydroxyapatite or du barium sulfate;

and, even more advantageously, a medium including bone mineral matrix including hydroxyapatite in the form of crystals.

and use instructions.

DETAILED DESCRIPTION OF THE INVENTION

Periostin is a protein from the extracellular bone matrix. It is composed of a constant main part and a shorter C-terminal part whose composition in amino acids is variable. This variability therefore leads to different isoforms.

In accordance with the invention, e.g. "periostin", designates all known isoforms of periostin without distinction, regardless of the modifications such as post-transductional modifications (carboxylation, glycosylation, acetylation, etc.) or others. In this presentation, we distinguish periostin or total periostin, carboxylated periostin—hereafter called "CP"—, undercarboxylated periostin or decarboxylated—hereafter called "UCP"— . . . . For lack of precision, the term "periostin" designates total periostin.

The terms "peptide", "polypeptide" and "protein" will be interchangeable and they mean any chain of amino acids linked to each other independently of the length of the chain and its post-transductional modifications.

PS Detection Sequences

The detection sequences according to the PS invention include from 6 to 30 (preferably 15 to 26) amino acids and include all or part of peptide sequence SEQ ID no. 1, SEQ ID no. 2 or SEQ ID no. 3, or a similar peptide sequence.

In a special embodiment, the PS detection sequences according to the invention are constituted of 6 to 30 (preferably 15 to 26) amino acids and include all or part of peptide sequence SEQ ID no. 1, SEQ ID no. 2 or SEQ ID no. 3, or a homologous peptide sequence.

These PS sequences make it possible to detect the total periostin without distinguishing the various isoforms of this protein. These sequences come from the constant part of periostin. These are short, very exposed and highly preserved peptide sequences among the various species, particularly between humans and mice. These given detection sequences and their homologs enable the early and reliable detection of biological phenomena or pathologies involving periostin without being limited to a particular isoform of periostin.

These new [specific] PS detection sequences of periostin and their homologs include all or part of the three annexed original sequences: SEQ ID no. 1, SEQ ID no. 2 and SEQ ID no. 3. SEQ ID no. 1 is fully in the periostin of humans, rats, mice, monkeys, etc., as shown from the annexed peptide sequences: SEQ ID no. 4 to SEQ ID no. 54 (FIGS. 2A-2H).

SEQ ID no. 2 is specific to human periostin (SEQ ID no. 4).

SEQ ID no. 3 is specific to murine periostin (SEQ ID no. 5).

| Reference Number SEQ ID | Reference of the protein sequence in the database NCBI |
| --- | --- |
| SEQ ID no. 6 | XP_001512245 |
| SEQ ID no. 7 | XP_001085920 |
| SEQ ID no. 8 | XP_001085575 |
| SEQ ID no. 9 | XP_001085814 |
| SEQ ID no. 10 | XP_001085700 |
| SEQ ID no. 11 | XP_001148441 |
| SEQ ID no. 12 | XP_001148156 |
| SEQ ID no. 13 | XP_001148083 |
| SEQ ID no. 14 | XP_001148381 |
| SEQ ID no. 15 | XP_001148299 |
| SEQ ID no. 16 | XP_001148230 |
| SEQ ID no. 17 | XP_001148006 |
| SEQ ID no. 18 | XP_001147936 |
| SEQ ID no. 19 | XP_001147873 |
| SEQ ID no. 20 | XP_509634 |
| SEQ ID no. 21 | XP_001147730 |
| SEQ ID no. 22 | BAA02836 |
| SEQ ID no. 23 | NP_006466 |
| SEQ ID no. 24 | AAN17733 |
| SEQ ID no. 25 | CAH70104 |
| SEQ ID no. 26 | CAH70105 |
| SEQ ID no. 27 | CAH70106 |
| SEQ ID no. 28 | AAY15840 |
| SEQ ID no. 29 | Q15063 |
| SEQ ID no. 30 | EAX08592 |
| SEQ ID no. 31 | XP_534490 |
| SEQ ID no. 32 | XP_856272 |
| SEQ ID no. 33 | XP_856313 |
| SEQ ID no. 34 | XP_856355 |

| Reference Number SEQ ID | Reference of the protein sequence in the database NCBI |
|---|---|
| SEQ ID no. 35 | XP_001495882 |
| SEQ ID no. 36 | XP_001495899 |
| SEQ ID no. 37 | XP_001495863 |
| SEQ ID no. 38 | XP_001495934 |
| SEQ ID no. 39 | NP_001035569 |
| SEQ ID no. 40 | NP_056599 |
| SEQ ID no. 41 | AAH31449 |
| SEQ ID no. 42 | BAC27122 |
| SEQ ID no. 43 | Q62009 |
| SEQ ID no. 44 | AAT48882 |
| SEQ ID no. 45 | BAE32339 |
| SEQ ID no. 46 | EDL35258 |
| SEQ ID no. 47 | EDL35259 |
| SEQ ID no. 48 | EDL35260 |
| SEQ ID no. 49 | EDL35261 |
| SEQ ID no. 50 | EDM14934 |
| SEQ ID no. 51 | EDM14935 |
| SEQ ID no. 52 | EDM14936 |
| SEQ ID no. 53 | EDM14937 |
| SEQ ID no. 54 | NP_001102020 |

In accordance with the invention, we designate e.g. "homologous sequence", as a sequence that has several variations with respect to the original sequence, here SEQ ID no. 1, SEQ ID no. 2 or SEQ ID no. 3. These variations come from the fact that in proteins, there can be deletions, additions, substitutions and/or insertions of one or more amino acids but without them significantly affecting the structure and the function of the protein integrating said sequence, in this case periostin. The latter thus preserves its activity (such as enzymatic activity) and/or its 3-dimensional folding. According to this invention, substitutions are defined e.g. as exchanges in one of the following groups:
  small aliphatic residue, non-polar or weakly polar: Ala, Ser, Thr, Pro, Gly
  residue loaded negatively, polar and their amide: Asp, Asn, Glu, Gln
  residue loaded positively, polar: His, Arg, Lys
  large aliphatic residue, non polar: Mand, Leu, Ile, Val, Cys
  large aromatic residue: Phe, Tyr, Trp.

Thus changes from a substitution of a residue negatively loaded by another (such as glutamic acid by aspartic acid) or a residue positively loaded by another (such as Lysine by Arginine) or post-transductional modifications such as glycosylation, nitration, isomerization, etc. can give equivalent products at the functional and three-dimensional level.

According to the invention, a sequence is called "homologous" of SEQ ID no. 1, SEQ ID no. 2 or SEQ ID no. 3, if its degree of homology with SEQ ID no. 1, SEQ ID no. 2 or SEQ ID no. 3, is, accordingly to an increasing index preferably, greater than or equal to 80%, 85%, 90%, 95%, and 97%.

The position over which on which the amino acids are modified and the number of amino acids subject to a modification in the sequence of amino acid SEQ ID no. 1, SEQ ID no. 2 or SEQ ID no. 3 is not limited. A person skilled in the art is capable of recognizing modifications that may be introduced without affecting the activity and/or the folding of the protein. For example a modification in the terminal N or C region of a protein is supposed not to alter the functional activity or the folding of the protein in certain circumstances.

In a preferred embodiment, PS corresponds to SEQ ID no. 1.

This sequence SEQ ID no. 1 is a peptide sequence of periostin highly preserved. In effect, SEQ ID no. 1 (whose sequence is KGFEPGVTNILKTTQGSK) is kept with 100% of homology between mice, humans and numerous other species such as monkeys, dogs, horses, rats (FIGS. 2A-2H).

In a second preferred embodiment, PS corresponds to SEQ ID no. 2.

In a third preferred embodiment, PS corresponds to SEQ ID no. 3.

These sequences: SEQ ID no. 2 and SEQ ID no. 3 are peptide sequences of periostin highly preserved. SEQ ID no. 2 (whose sequence is ETLEGNTIEIGCDGDSI) is specific to human periostin (SEQ ID no. 4) and SEQ ID no. 3 (whose sequence is EAITGGAVGEAITGGAV) is specific to murine periostin (SEQ ID no. 5) that contains the monomeric sequence EAITGGAV.

The PS detection peptide sequence(s) according to the invention is a peptide that can exist as such or be included in a longer (poly)peptide.

Thus, according to the invention, the expression "PS detection peptide sequence(s)" also covers any immunogenic (poly)peptide including PS as defined in this application and involving more than 30 amino acids.

As will be seen below, PS as well as any immunogenic (poly)peptide including PS allows the production of specific antibodies, in particular directed against all or part of peptide sequence SEQ ID no. 1, SEQ ID no. 2 or SEQ ID no. 3, or a sequence homologous to one of said sequences.

According to a special embodiment, this invention concerns an antigen of peptide sequence PS consisting of 6 to 30 amino acids (preferably 15 to 26) and including all or part of peptide sequence SEQ ID no. 1, SEQ ID no. 2 or SEQ ID no. 3, or a homologous peptide sequence.

Advantageously, PS is isolated from its natural or produced environment with help from a technical process.

Here, "isolated", means e.g. a peptide sequence or a protection that has been separated or purified of compounds that accompany it in its natural medium, for example, in its original tissue such as the bone, the heart, a tumor tissue, or a body liquid such as blood, the lymph, urine, saliva. According to this invention, peptide sequence PS en question is preferably isolated from the bone and preferably from the periostea.

An isolated peptide sequence according to the invention can be obtained, for example, by extraction from its natural source (such as body tissues or liquids); by expression by a recombinant nucleic acid coding for said peptide sequence; or by chemical synthesis. the degree of separation/purification of said peptide sequence can be verified by various methods known by a person skilled in the art such as column chromatography, high-performance liquid chromatography analysis (HPLC) or by electrophoresis on polyacrylamide gel.

PS can also be produced using a known technical process, e.g.: peptide synthesis, genetic synthesis, or a technique like the one described in "*Ed Harlow and David Lane 'Antibodies: a laboratory manual' Cold Spring Harbor Laboratory press* 1988".

Nucleic Sequences Coding for Peptide Sequences (PSes) for Detection [Detection Peptide Sequences]

The invention also concerns a gene synthesis tools of peptide sequences (PSes), in particular of sequences: SEQ ID no. 1, SEQ ID no. 2 or SEQ ID no. 3, or their homologous sequences. These gene synthesis tools are nucleic sequences minimally coding periostin detection sequences (PSes) as defined above, including the aforementioned "immunogenic (poly)peptides".

The nucleic sequences in question can be DNAc sequences, DNA genome sequences or synthetic or RNA sequences. They can be single or double strand. These sequences can be produced by PCR or using restriction enzymes. These sequences can also contain sequences that differ from those naturally generated but due to the degenerescence of the genetic code, still make it possible to code the same protein sequence and in particular a sequence containing SEQ ID no. 1, SEQ ID no. 2 or SEQ ID no. 3, or a sequence homologous to the aforementioned sequences with a degree of homology as defined above. These nucleic sequences are obviously not limited to only coding sequences, they can contain non-coding sequences.

One will have understood that due to the nucleic sequences described above, by known protein isolation or production processes, peptide sequences will have been obtained that are isolated from their natural environment or artificially produced as described above and that these peptide sequences correspond to immunogenic peptides capable of engendering creating the formation of specific antibodies.

Means of Periostin Detection: Antibodies

In accordance with the invention, detection peptide sequences (PSes) are excellent specific targets of periostin and observable in a periostin qualitative and/or quantitative analysis process.

It is therefore worthwhile appropriate to provide, in such a process, probes capable of recognizing said targets. This is another object of this invention, i.e., detection means of periostin, that include a specific recognition tool of one or more peptide sequences (PSes). This tool minimally involves an anti-periostin antibody and/or minimally one of its functional fragments (Ac anti-periostin), specific to SEQ ID no. 1, SEQ ID no. 2, SEQ ID no. 3, or a peptide sequence with a degree of homology greater than or equal to 80%, preferably greater than or equal to 85% minimally with regard to sequences: SEQ ID no. 1, SEQ ID no. 2 and SEQ ID no. 3.

The recognition tool specific to periostin is preferably an anti-periostin antibody or minimally one of its functional fragments. In a special embodiment, the antibody according to the invention is minimally directed against one of the sequences: SEQ ID no. 1, SEQ ID no. 2 or SEQ ID no. 3.

In this application, the term "antibodies" designates e.g. immunoglobulins (Ig), for example, Gamma—(Ig G) or Mu—(Ig M), preferably IgG-type immunoglobulins. These antibodies can be polyclonal or monoclonal. These are from the immunization of animals such as rabbits (polyclonal), mice (monoclonal) and all animals that are immunized and known to a person skilled in the art but they can be produced by genetic engineering. Moreover, the antibodies according to the invention can be natural or humanized animal-origin antibodies (preferably from rabbits or mice). By extension, antibodies according to this invention can be one of the functional fragments of said antibodies such as the fragment Fv, the fragment Fab that contains the site of recognition specific to the antigen, the fragment F(ab')$_2$ that minimally contains the two recognition sites specific to the antigen. It can also involve chimera antibodies.

In this application, the term "epitope" designates e.g. a molecule or a region thereof that can be recognized by the specific recognition part of an antibody (the paratope). An antigen is characterized by its epitopes.

Thus, in accordance with the invention, the antigens likely to be recognized and are complexed with the detection means of periostin, are PS sequences as defined in this presentation. Moreover, the corresponding epitopes are notably peptide sequences (PSes) from 6 to 30 amino acids corresponding in all or part to SEQ ID no. 1, SEQ ID no. 2 or SEQ ID no. 3, or to a sequence homologous to one of them. They are known to the person skilled in the art that an antigenic site generally contains 5 to 20 amino acids but according to a preferred mode of the invention, the specific antigenic epitope recognized by the antibody can contain a lower number of amino acids, i.e., from 6 amino acids to 16 amino acids without being limited to this number. The epitope preferably contains 12 amino acids.

"Specific", means e.g. in accordance with this presentation that the antibodies recognize and link to a given epitope via their paratope according to known principles of immunology. In particular, the recognized antigen is defined by its particular epitope according to the structure or the conformation thereof.

Thus, the antibodies according to this invention make it possible to specifically recognize all the isoforms of periostin containing SEQ ID no. 1, SEQ ID no. 2 or SEQ ID no. 3, or a sequence homologous to one of these sequences.

Production Process of Detection Means (Antibodies) of Periostin

This process according to the invention includes the stages abcde(f) defined above and detailed below.

Stage a:

More specifically, and according to a first $1^{st}$ advantageous method embodiment of the invention making it possible to generate these specific antibodies of periostin via the epitope of sequence SEQ ID no. 1 or a sequence homologous to that as described above, it is provided to use for example a peptide sequence derived from the sequences of human periostin SEQ ID no. 4, murine SEQ ID no. 5 and any other sequence cited SEQ ID no. 6 to SEQ ID no. 54 (FIGS. 2A-2H) artificially produced and including at least SEQ ID no. 1 or a sequence homologous to it. This isolated or artificially produced peptide sequence mimics the identical region or homologous of native periostin or of an isoform.

More specifically and according to a second $2^{nd}$ advantageous embodiment method of the invention making it possible to generate these specific antibodies of periostin via the epitope of sequence SEQ ID no. 2 or a sequence homologous to it as described above, it is provided, for example, a peptide sequence derived from the sequences of human periostin SEQ ID no. 4, SEQ ID no. 22 to SEQ ID no. 30.

More specifically and according to a $3^{rd}$ advantageous method of the invention making it possible to generate these specific antibodies of periostin via the epitope of sequence SEQ ID no. 3, or a sequence homologous to it as described above, it is provided to use for example a peptide sequence derived from the sequences of murine periostin SEQ ID no. 5, SEQ ID no. 40 to SEQ ID no. 49.

Stage b:

Once the antigen produced or isolated (stage a), it is coupled to a carrier protein. The term "coupled" means for example linked or conjugated. This link or conjugation can be made chemically, for example by a covalent link, adsorption or another method of binding known to a person skilled in the art. Preferably, the coupling is performed by a coupling agent such as carbodiimide or glutaraldehyde.

The carrier molecule to which the antigen is coupled is a molecule of molecular weight sufficient important to induce an immune reaction and the production of circulating antibodies. This molecule can be a protein, a natural or synthetic polymer. It is preferably a protein and in particular a protein with a molecular weight greater than or equal to 5 kDaltons such as Bovine Serum Albumin (BSA), ovalbumin, Keyhole Limpet Hemocyanin (KLH). In a preferred form of the invention, the protein KLH will be used as carrier protein.

Stage c:

The antigen-carrier molecule pair is injected to animal to be immunized. The antigen-carrier molecule pair is preferably in suspension and preferably mixed with a Freund's adjuvant solution that is composed of mineral oil plus an emulsifying agent (incomplete adjuvant) and inactivated bacillus particles of the tuberculosis (complete adjuvant). The animal into which said antigen-carrier molecule pair is injected in suspension may be a rabbit, a mouse, a rat, a goat, a lamb, a horse or a hamster, preferably a rabbit, rat or mouse. The said pair can be injected at a single time or several times according to the classical and known methods of immunization. The principal paths of administration are sub-cutaneous, intradermal, or intramuscular injections; intravenous and intra-peritoneal injections are only used in special cases. If there are several injections of the antigen-carrier molecule pair, the types of antibodies produced, specific to the antigen as defined above, are different. In effect, it can involve type-G or -M immunoglobulins. The injection methods are known and are classical methods in the immunization protocols of animals, particularly, rabbits. Thus, one preferably makes an intramuscular injection of approximately 0.5 to 1 mg of said antigenic pair to a rabbit and approximately 50 to 100 µg to a mouse.

The blood of the animal—containing among other things, antibodies specific to the injected antigen—is recovered by blood sampling or by exsanguination. Preferably, plasma or serum—containing among other things antibodies specific to the antigen as defined above—is also taken. The serum containing the desired antibodies, directed against said antigen, normally contains several species of different antibodies directed against several epitopes of the same antigen; this preparation is called polyclonal. It is also possible to use techniques making it possible to isolate and clone lymphocytes only producing a molecular species (i.e., clonotype) of antibodies: antibodies that only recognize a single epitope of the antigen.

Stage d:

The selection stage (or titration) of the antibodies specific to said antigen as defined above is performed using the Enzyme-Linked Immuno Sorbent Assay (ELISA) technique. This selection technique is widely described in literature.

Stage e:

This optional purification stage of antibodies can be carried out in liquid or solid phase. There are various ways to determine the affinity chromatography by using either separation columns, magnetic beads or resins carrying said antigen as ligand. A solid medium such as a sepharose column is preferred on which the antigens have been bound, preferably by covalent link. The blood/blood/plasma/serum is made to pass over said binding column where only antibodies against the antigen should bind themselves on the column; all of the other proteins of the serum are washed in the eluate allowing the selection of antibodies specific to the antigens.

Process of Detection and Possibly of Dosage of Total Periostin in a Biological Sample This invention gives access to PS detection sequences, which make it possible to produce detection means comprised e.g. of a periostin recognition tool, preferably anti-periostin antibodies. This specific tool makes in vitro detection possible (quantitative analysis) and even perhaps the dosage (quantitative analysis) of total carrier periostin of all or part of PS, by the process defined above and involving stages I-II-III-(IV).

The PS periostin detection sequences as defined in this presentation are particularly advantageous as they make it possible to distinguish, quantify and/or locate the periostin expressed in the organism without distinguishing its various isoforms (5) that have been listed heretofore (FIGS. 2A-AH), or post transductional modifications such as carboxylation, glycosylation, etc.

The detection and/or quantification (concentration) of the protein marker that periostin is, via PS detection sequences according to the invention, in a biological sample of a subject (animal or human) is particularly interesting since it provides an early and reliable indication of the non-pathological biological phenomena that are produced in certain tissues in this individual, in particular the bone, but also of any pathologies involving periostin. It thus constitutes a major index either of the physiological condition of a subject at the bone metabolism level, in particular of the periostea and/or cartilage, notably during growth or during andropause or menopause, or the pathological state of the individual who has been attacked by or is prone to illnesses involving periostin, notably bone pathologies such as osteoporosis, bone metastases of breast and prostate cancer and of other origins, myeloma, or osteoarticular pathologies such as arthrosis, rheumatoid polyarthritis, spondyloarthritis, fibroses (notably hepatic), and cardiovascular diseases.

The invention therefore provides significant technical progress through this specific, reliable and easy-to-use periostin marker recognition and detection tool; this tool constitutes the basis of the process under this heading and specifications are provided below regarding its stages. Within this framework, the detection of the antigen-antibody complex can be broken down according to several technologies such as ELISA, EIA or RIA tests, immunoturbidimetry, latex on blade agglutination of, nephelometry, turbidimetry, turbidimetry or nephelometry amplified by latex particles, immunohistochemistry/colorimetric cytochemistry, immunofluorescence (on blade), microplate, latex fluorescent, magnetic latex, test on membrane, biochips etc.), western blot, dot blot, high-performance liquid chromatography (HPLC), by electrophoresis, by spectroscopy, or by proteomic or "microarray" analysis techniques, and generally any process can be used that makes it possible to identify and/or quantify a reaction between an antigen and more particularly an epitope and an antibody, regardless of the isotype. Preferably, an ELISA test is used. In a particular embodiment of the invention, the periostin detection process consists of an ELISA dosage, preferably a "competitive" or "sandwich" ELISA dosage.

In a variant, techniques can be used allowing the direct detection of antibodies as antibody-epitope complexes such as refractometry, the diffraction of light rays by the reaction surface, methods for modifying electrical conductivity or the magnetic field, etc.

Immunochemistry methods of detection generally use an enzyme reaction (peroxidase, glucose oxidase, alkaline phosphatase). Preferably, the immunological reaction, i.e., the recognition of the antibody or of at least one of its functional fragments according to the invention with the antigen as defined above, is followed by an indicator reaction that produces a colored signal amplified by enzymes and their chromogen substrates or that allows the photometric detection, fluorescent or radioactive electrochemistry etc. of the enzyme activity linked to the concentration of the antibody-antigen complex.

These generic techniques can also fall under the following stages

Stage I:

Under the invention, the term "biological sample" designates any type of sample, useable in vitro, of any substance likely to contain said antigen in question corresponding to a peptide sequence (PS), i.e.:

a liquid substance such as serum, plasma, blood, lymph, urine, saliva, the surnatant of cells placed in culture, bone marrow, an organ homogenate, cytoplasmic extracts of given cells;

or a solid substance, for example cuts from tissues (for example bone or tumor), an organ or a cut thereof.

These samples are taken from animals or healthy or ill patients, for example, breast or prostate cancer patients.

Preferably, serum is used.

Antibodies can be previously bound (sandwich technique) or not (competition technique) to a suitable support.

Immunological reaction supports of different types can be used and are chosen from among: blades, microplates, fluorescent latex, magnetic latex, immune-filtration membranes or immune-migration membranes, biochips, beads, fins, tubes but also liposomes, lipid vessels, biological microparticles or obtained from polymers, emulsions or any other support known to a person skilled in the art and adapted for the implementation of said processes.

Washes can be used to eliminate non-specific bindings or unbound products in excess. According to methods known to a person skilled in the art, the specific antibody can be used in liquid phase or in solution. Preferably, the recognition tool of the detection sequence (antibodies or one of their functional fragments) according to this invention is previously bound on an essentially solid support or any reaction support making it possible to conduct an immunological test. Binding to the support is preferably performed by adsorption or a covalent link. A wash stage makes it possible to eliminate—after binding—antibodies not bound to said support, if applicable.

Stages II-III-(IV):

When the sample contains molecules minimally containing this antigen, periostin molecules, the latter via the epitope will bind to the antibodies that can be bound beforehand (sandwich technique) or not (competition technique) to an adapted support.

Thus, periostin detection makes it possible to determine the expression level of this protein and, considering the fact that the antibody is directed against a very exposed epitope in the common part of periostin, this detection process makes it possible to determine the expression level of total periostin, all forms together of the protein. The implementation of this detection process, due to the PS detection sequences according to the invention and the antibody as defined above, is particularly interesting, since it will make it possible to better understand or define the roles of periostin in certain biological processes since this protein of the excellular matrix of the periostea is involved in various metabolisms and as yet poorly understood biological and pathological phenomena. Thus, this detection process makes it possible to better define, understand and determine—among other things—the metabolic activity of the bone during the life of a given individual. Since periostin is strongly expressed at the periosteum level and the periostea is a structure whose role is crucial for bone solidity, this protein has been conceived of being used as a marker of the metabolic activity of the periostea. Thus, the expression level of this marker may be an indicator of the action of hormones or therapeutic agents on the periostea. Contrary to the involvement of periostin in cancer mechanisms, no publication has yet noted its usefulness as a marker of the bone remodeling, and more specifically of the periosteum metabolism.

In a variant of an embodiment, the periostin detection process, in an in vitro biological sample, is based on the competitive ELISA dosage technique and includes the following stages:

I'. Bind on an appropriate support a synthetic biotinylated peptide PS antigen including all or part of the epitope contained in PS and in particular in SEQ ID no. 1, SEQ ID no. 2 SEQ ID no. 3 and/or in a sequence homologous thereto, the degree of homology being as defined above, II'. Place said support of stage I in the presence of, on one hand, a biological sample susceptible of containing the periostin and, on the other, antibodies directed against minimally one of said peptides PS as described above or one of their functional fragments, II'.1. Minimally perform one wash, III'. Reveal any Ac anti-periostin/PS complexes formed, IV'. Dose any Ac anti-periostin/PS complexes formed by means of the marking or of the optical density to deduce the concentration of periostin contained in the sample. The weaker the optical density, the more periostin the biological sample contains.

In another variant of the embodiment, the periostin detection process, in an in vitro biological sample, is based on the sandwich ELISA technique and includes the following stages:

I". possibly bind on an appropriate support the antibodies or minimally one of their functional fragments as defined above, II". Place said antigen corresponding to all or part of the PS and in particular of SEQ ID no. 1, SEQ ID no. 2 SEQ ID no. 3 and/or a sequence homologous to a sequence thereof, in the presence of a sample possibly containing said with the antibodies or minimally one of their functional fragments as defined above, II".1. minimally perform one washing, III". detect/reveal the antibody-antigen complexes as may be formed.

Detection and Dosing Process of Undercarboxylated Periostin (UCP), to be Distinguished from Carboxylated Periostin (CP)

This process defined above includes stages $I^{UCP}$ $I^{UCP}.1$ $I^{UCP}.2$ $I^{UCP}.3$ $II^{UCP}$ $III^{UCP}$ $IV^{UCP}$ The PS detection sequences and the means for the associated detection (recognition tool of PS—preferably antibodies—), also make it possible to detect and of dose special CP and UCP forms of periostin. In effect, it is to the credit of the inventors that they observed that the carboxylated periostin (CP) shows more affinity for certain binding supports and in particular for hydroxyapatite (preferably in crystals) that enters into the constitution of the mineral matrix of the bone.

Below a preferred embodiment is described.

Stage $I^{UCP}$.:

$I^{UCP}.1$—The biological sample containing the periostin is first placed in contact with crystals of hydroxyapatite.

$I^{UCP}.2$—The sample is first stirred and then centrifuged.

$I^{UCP}.3$—The surnatant containing the UCP periostin is recovered.

$I^{UCP}$. This surnatant is placed in the presence with detection means according to the invention: Ac anti-periostin.

$III^{UCP}$. Any Ac anti-periostin/PS complexes formed are isolated;

$IV^{UCP}$. These Ac anti-periostin/PS complexes formed are dosed to deduct the concentration of UCP periostin in the surnatant, and lastly, in the sample.

The rate of CP periostin is determined indirectly, i.e., that it corresponds to the difference between the rate of total periostin (determined by dosing the biological sample that did not undergo the treatment) and the rate of UCP periostin (determined by the dosing the biological sample treated with the hydroxyapatite as mentioned above).

In other words, this CP periostin detection and dosing process essentially consists of 1. preparing a biological sample,
2. dosing the total periostin in this biological sample,
3. dosing the UCP periostin in this biological sample,
4. making the difference between the concentration in total periostin and the concentration in UCP periostin in this biological sample, in order to obtain the concentration in CP periostin in this biological sample.

Barium sulfate can be notably cited by affinity as another binding support of CP or of UCP. Processes for determining the expression level of total periostin and undercarboxylated are preferably performed directly by ELISA with antibodies as defined in this application, directed against all or part of SEQ ID no. 1, SEQ ID no. 2 or SEQ ID no. 3, or one of their homologous sequences with a degree of homology vis-à-vis one of the aforementioned sequences as defined above.

The periostin carboxylation rate has an impact on certain pathologies; accordingly, the determination of these two periostin (carboxylated and undercarboxylated) rates may prove to be crucial in the diagnosis, tracking or prognosis of pathologies.

The inventors have been able to detect carboxylated forms of periostin in the serum of healthy patients. They have also observed an increase in the serum rates of total periostin in prostate cancer patients with bone metastases and an increase in serum rates of carboxylated periostin in the same patients, in comparison with healthy patients.

It therefore appears that the processes and means according to this invention (detection sequence and/or recognition tool of PS detection sequences, preferably anti-periostin antibodies) are used in order to essentially determine:

the expression level of total periostin (without distinguishing isoforms or post-transductional modifications such as carboxylation, glycosylation, nitration, isomerization, etc.;
the expression level respectively of decarboxylated periostin and of carboxylated periostin (indirectly) with respect to the expression level of total periostin;
the metabolic activity of the periostea;
the remodeling level of the bone and/or joint cartilage;
  a) related to age;
  b) related to a hormonal change;
  c) related to physical activity;
  d) related to the presence of tumor cells;
the level of vascular mineralization;
the presence or absence of bone metastases, preferably of breast or prostate cancer bone metastases;
the stromal response level to breast cancer bone metastases;
the presence or absence of reactions of fibrosis linked to tumors;

Applications of the Detection Process According to the Invention Under Examination of Biological Phenomena Involving Periostin, in the Diagnosis, Tracking or Prognosis of a Pathology Involving Periostin, or in Determining the Efficacy of a Medication Adapted to the Treatment of a Pathology Involving Periostin The means and processes according to the invention open numerous doors for the understanding and treatment of pathologies involving periostin, such as cancer, bone pathologies such as osteoporosis, bone metastases of breast and prostate cancer and of other origins, myeloma, or osteoarticular pathologies such as arthrosis, rheumatoid polyarthritis, spondyloarthritis, fibroses (notably hepatic), and cardiovascular diseases.

Moreover, in addition to its physiological role in the bone, numerous studies using in vitro and in vivo models have shown the involvement of periostin in various pathological mechanisms such as cancer. In effect, it is known that periostin interacts with cell adhesion proteins. It could have a role in cell invasion, tumor survival, angiogenesis and the metastatic potential of tumor cells. Moreover, periostin plays a role in osteoblastogenesis and could have an indirect effect on osteoblastogenesis, and accordingly, on malignant osteolysis that characterizes bone metastases. Thus, periostin detection, by means of at least one new detection sequence as previously defined and at least one means of recognition of a new detection sequence (preferably an antibody), is interesting in clinical studies aimed not only at diagnosing, tracking, providing a prognosis or follow-up treatment, etc. of bone metastases, osteoarticular pathologies, but also constitutes a new therapeutic approach to malignant osteolysis and to cartilage degradation.

Moreover, the inventors have been able to demonstrate that during injections of human breast cancer cells to a mouse, murine stromal cells express the periostin in response to the presence of human tumor cells. Thus, periostin dosage can be interesting in estimating its potential role in stromal reaction and thus allow very early periostin detection during bone metastatic processes before the reabsorption of the bone and therefore before the possible detection by imaging and before the detection of a modification in the dosage of the known bone remodeling markers.

It then follows that the invention also concerns:

i. an isolation and evaluation process of a non-pathological biological phenomenon involving periostin,
ii. a pathology diagnosis, tracking or prognosis process involving periostin,
iii. and a process for determining the efficacy of a medication adapted to the treatment of a pathology involving periostin, characterized in that it consists of implementing the process according to the invention as described above.

These processes (i), (ii) & (iii) more specifically and essentially consist of:

I. preparing a biological sample susceptible of containing periostin or coming from the subject who is being diagnosed, tracked, or for whom a prognosis is being provided of a pathology involving periostin or for determining the efficacy of a medication adapted to the treatment of a pathology involving periostin,
II. placing said biological sample in the presence of a recognition tool specific to periostin as previously defined, preferably an antibody or one of the functional fragments thereof as defined above, III. isolating the periostin by detecting possible immunological Ac anti-periostin/PS complexes as may be formed, IV. and possibly dosing these Ac anti-periostin/PS complexes formed to deduct the concentration of periostin in the sample.

According to an interesting method of the invention, it is anticipated in the process (i) that the phenomenon is chosen in the group of phenomena including:

The metabolic activity of the bone, in particular of the periostea, the remodeling of the bone and/or the joint cartilage as a function of age, hormonal change, physical activity, intermembrane ossification, the phenomenon of vascular mineralization.

Following another interesting method of the invention, it is anticipated in the process (ii), that at the end of the quantitative in vitro analysis (stages I-II-III-IV) of periostin present in a biological sample of a subject, the concentration of periostin measured in the sample is compared with a reference concentration corresponding to the existence or absence of pathology involving periostin in a control subject of the same species.

Preferably, the reference concentration corresponds to an absence of pathology, or to the existence of a pathology at a certain stage. This choice can be made by the person familiar with the art as a function of the marker selected and the technique used.

For example, the reference concentration that delineates the pathological state of the non-pathological state for different techniques, correspond to the value above the 95$^{th}$, preferably above the 97.5$^{th}$ percentile of the values of healthy or control subjects.

The pathology considered in processes (ii) & (iii), is e.g., chosen from the group of pathologies including:

bone pathologies preferably in the sub-group including osteoporosis, bone metastases of breast or prostate cancer or of other origins, myeloma, and fibrous dysplasia;

and osteoarticular pathologies preferably in the sub-group including arthrosis, rheumatoid polyarthritis, spondyloarthritis;

fibroses (notably hepatic) and les cardiovascular diseases.

A periostin detection and in vitro dosage kit, in a biological sample. This kit contains a certain number of useful elements for conducting the process described above of detection and in vitro dosage of total periostin, in a biological sample, to wit:

periostin detection means according to the invention, that are preferably Ac anti-periostin generated by means of PS sequences;

reagents and equipment for the detection, perhaps even the dosage, of any Ac anti-periostin/PS complexes formed, per stages III, or perhaps even IV, described above;

and use instructions.

The invention also targets a detection and dosage kit of undercarboxylated periostin (UCP) including:

periostin detection means;

reagents and equipment for the detection, perhaps even the dosage, of any Ac anti-periostin/PS complexes formed per stages III, or perhaps even IV described above;

a support for the implementation of stages I$^{UCP}$ And II$^{UCP}$ described above, i.e., a support suitable for binding CP preferably to UCP or conversely, said support being:

advantageously a support with an affinity to CP greater than the affinity to the UCP;

and, more advantageously, a support including hydroxyapatite;

and, of even more advantageously, a support including the bone mineral matrix including hydroxyapatite in the form of crystals;

and use instructions.

EXAMPLES

The following examples illustrate this application.

The invention will be better understood if one refers to the attached figures wherein:

FIG. 1 represents peptide sequences of SEQ ID no. 1, SEQ ID no. 2 and SEQ ID no. 3;

FIGS. 2A-2H represent the sequences of the isoforms (SEQ ID no. 4 to SEQ ID no. 54) and species in which sequence SEQ ID no. 1 is present with 100% of homology, and human sequences: SEQ ID no. 4 and murine sequences: SEQ ID no. 5 with which sequences: SEQ ID no. 2 and SEQ ID no. 3 show 100% of homology, respectively;

FIG. 3 shows titration curves to determine the concentration in antibodies specific to the peptide of sequence SEQ ID no. 1 as a function of the quantity of biotinylated peptide (SEQ ID no. 1) bound to the plate (FIG. 3A) and a titration curve of the antiserum for various concentrations of peptide (SEQ ID no. 1) adsorbed on the ELISA plate (as indicated);

Example 1

Figure 4:
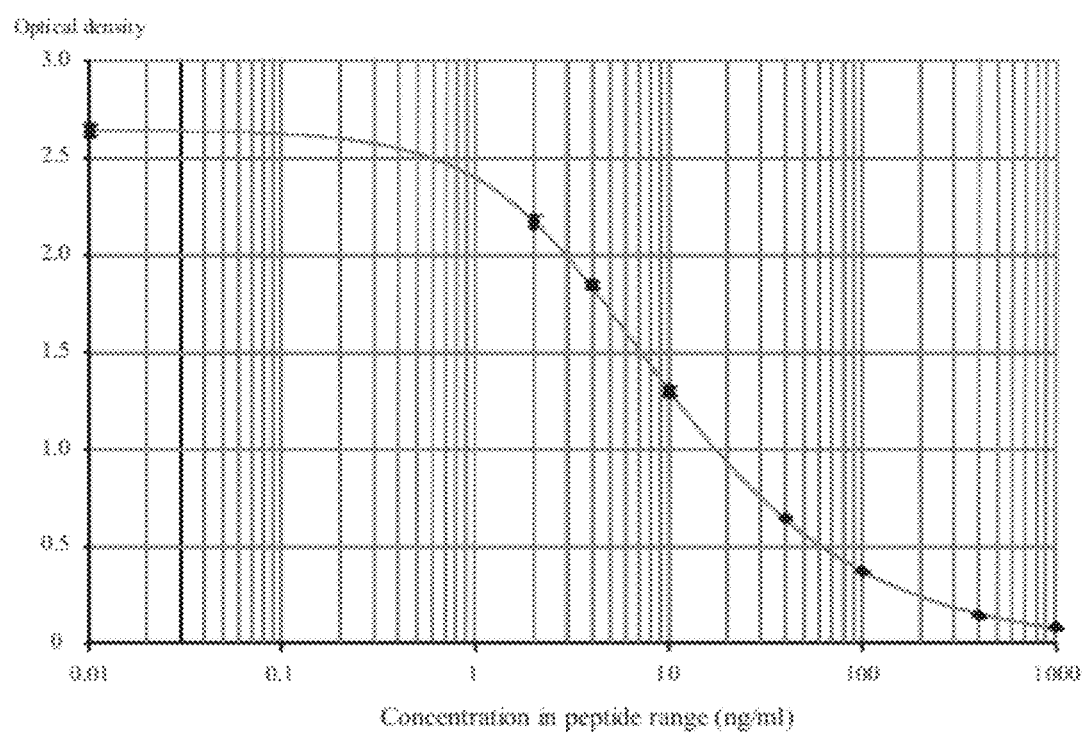
FIG. 4 represents the standard dosage curve by ELISA of the peptide containing SEQ ID no. 1.

Production Process of the Anti-Periostin Antibody According to the Invention

1. Computer Analysis for Identifying the Immunogenic Peptide Sequence, Detection Sequence of Periostin.

The computer selection is based for each protein on:

a—Prediction of accessibility of the detection sequence:

prediction of accessibility of the sequence to a solvent based on the sequence of amino acids;

prediction of the secondary structure;

prediction of a trans-membrane domain;

an analysis of the surface accessibility, if a 3-dimensional model is available;

b—Antigenicity: evaluation of the presence of antigenic determinants at the protein sequence level of periostin detection:
   a prediction of the antigenicity based on characteristics of the sequence of amino acids;
   an analysis of the parameters influencing the antigenicity (possibility of mutations, flexibility, post-transductional modifications);
   c—Analysis of the potential of cross reactivity:
   search for inter-species homologies;
   search for short inter-species similarities;
   d—Application of a selection method integrating the previous information for selecting 3 to 5 peptides (approximately 17 amino acids).

2. Preparation of the Immunogenic Peptide Sequence, of Periostin Detection Minimally Containing SEQ ID no. 1(Stage a)

The peptide of sequence SEQ ID no. 1, derives from the periostin sequence (GenBank accession number: Q15063) was produced by the technique of peptide synthesis on solid phase by using a reversible blocking of the amine of the amino acid by the Fmoc (9-fluorenylmethyloxycarbonyl). The purity of the peptide was verified by HPLC and by mass spectrometry.

3. Pairing of the Immunogenic Peptide Sequence of Periostin Detection to a Carrier Protein (Stage b)

The peptide serving as an immunogen, synthetized with an extra cysteine of the C-terminal side, is paired on the C-terminal side to a carrier protein that is the keyhole limpet Hemocyanin (KLH) which will allow a better immunological response to this peptide. The synthetic peptide that is adsorbed on microplates was paired to the biotin (Harlow and Lane, 1988).

4. Injection of said Antigen-Carrier Molecule Pair to an Animal and Recovery of the Blood/Serum (Stage c)

2 rabbits received 4 intra-peritoneal and subcutaneous injections on days D0, D14, D28 and D58 of 1 ml of a mixture (50%/50%) of a solution containing 200 μg of peptide conjugated with the KLH and Freund's adjuvant according to the immunization protocol in the table below (stage c). Regular blood samples were taken (on D0, D36, D70 and D90) to check the immune response (stage d and e). This blood was left to coagulate for 30 minutes then centrifuged for 10 minutes at 2500 rpm in order to recover the serum and test the immuno-reactivity of the antibodies.

| Day | Protocol |
| --- | --- |
| 0 | T0: Sampling of control serum (4-5 ml) and preservation at +4° C. |
| 0 | Subcutaneous injection (1 ml/rabbit) 0.5 ml Antigen + 0.5 ml complete Freund's adjuvant |
| 14 | Subcutaneous injection (1 ml/rabbit) 0.5 ml Antigen + 0.5 ml incomplete Freund's adjuvant |
| 28 | Subcutaneous injection (1 ml/rabbit) 0.5 ml Antigen + 0.5 ml incomplete Freund's adjuvant |
| 36 | T1: Sampling of test serum (4-5 ml) and conservation à +4° C. |
| 58 | Subcutaneous injection (1 ml/rabbit) 0.5 ml Antigen + 0.5 ml incomplete Freund's adjuvant |
| 70 | T2: Sampling of test serum (15 ml) and preservation at +4° C. |
| 90 | T3: Final sampling and preservation at +4° C. |

5. Selection of Specific Antibodies of the Epitope in the Serums: Titration of the Antiserums (Stage d)

Specific anti-periostin antibodies are selected in the serum with the synthetic peptide sequence antigen minimally including one sequence of 6 to 30 amino acids minimally containing sequence SEQ ID no. 1 produced above by determining the immunoreactivity of the rabbit serum using the ELISA technique. The antiserum with the best titer was selected to adjust the competitive ELISA (Harlow and Lane, 1988).

The titers of the antiserums were prepared by adsorbing the antigenic peptide conjugated to the biotin diluted with coating buffer on plates coated with streptavidin (Nunc, Danemark) for 2 hours at ambient temperature. The biotinylated antigenic peptide is diluted to 0; 2; 5; 10; 15 and 50 ng/ml. After washing, 50 μl of antiserums diluted from 1/100 to 1/1,000,000 are added to 50 μl of dilution buffer in the well and are incubated for 2 hours at ambient temperature. After washing, 100 μl of secondary antibodies, coupled to the peroxidase, directed against the rabbit immunoglobulins are added for one hour at ambient temperature. The wells are washed and 100 μl of substrate (TMB) are added. The reaction is stopped with 100 μl of $H_2SO_4$.

FIG. 3A illustrates this titration of the antiserum containing the antibody directed against the peptide of periostin detection containing SEQ ID no. 1. The x axis shows the various dilutions of the antiserum (from 0 to 1/16384000) and the y axis shows the optic density at 450 nm.

FIG. 3B illustrates the ratio between the concentration of coated biotinylated peptide and the dilution in antibodies. IC 50 is the dilution of the antibody corresponding to 50% of the maximum optical density obtained with the strongest concentration of antibodies, therefore, the smallest dilution. The coating at 10 ng/ml will be chosen since the plateau phase was reached at this concentration. The IC50 for a coating at 10 ng/ml is 197800.

6. Purification of Antibodies (Stage e)

The immuno-purification stages of the antibodies are carried out in accordance with the protocols described in the publication of Thomas V et al in J Immunol Methods. 2004 September; 292 (1-2):83-95.

Example 2

Competitive ELISA for Periostin via the Detection Sequence SEQ ID No. 1

Peptide minimally containing SEQ ID no. 1 conjugated to the biotin diluted with coating buffer is adsorbed on plates, coated with streptavidin, for 2 hours at ambient temperature. After washing, 50 μl of antiserums (rabbit) diluted at the optimal titer are added to 50 μl of standard (synthetic peptide diluted in buffer) or to 50 μl of dose samples susceptible of containing periostin and are incubated for 2 hours at ambient temperature. After washing, 100 μl of secondary antibodies coupled to peroxidase directed against rabbit immunoglobulins are added for one hour at ambient temperature. The wells are washed and 100 μl of substrate (TMB) are added. The reaction is stopped with 100 μl of $H_2SO_4$.

By refining the titer by a displacement test, a titer of 180000 is obtained and the various points of the standard range are determined. A standard or calibration curve was obtained on a semi logarithmic chart by dosing the 7 standards (from 1.33 to 1000 ng/ml) with the antiserum directed against sequence SEQ ID no. 1 selected for its titer (FIG. 4). The periostin concentration in the samples is obtained by extrapolation of the calibration curve. The limit detection of this test was determined by calculating the average of 20 determinations of the standard 0 from which the standard deviation is deducted three times. The detection limit is 0.39 ng/ml.

The analytic performance of the ELISA was checked by conducting:

1) dilution tests: a serum sample is dosed pure and diluted (cf. Table 1).

TABLE 1

Dilution tests of 3 serums in the dosage of periostin by ELISA

| | Dilution percentage of the serum | Concentration of periostin (ng/ml) | Recovery (%) 1-(expected value − measured value/expected value) | | | | | | | | |
|---|---|---|---|---|---|---|---|---|---|---|---|
| A | 100% | 20.53 | 100 | | | | | | | | |
| | 90% | 20.38 | 110 | 100 | | | | | | | |
| | 80% | 22.00 | 134 | 121 | 100 | | | | | | |
| | 70% | 19.44 | 135 | 123 | 101 | 100 | | | | | |
| | 60% | 18.76 | 152 | 138 | 114 | 113 | 100 | | | | |
| | 50% | 17.01 | 166 | 150 | 124 | 122 | 109 | 100 | | | |
| | 40% | 12.84 | 156 | 142 | 117 | 116 | 103 | 94 | 100 | | |
| | 30% | 9.93 | 161 | 146 | 120 | 119 | 106 | 97 | 103 | 100 | |
| | 20% | 5.43 | 132 | 120 | 99 | 98 | 87 | 80 | 85 | 82 | 100 |
| | 10% | 1.18 | 58 | 52 | 43 | 43 | 38 | 35 | 37 | 36 | 44 |
| B | 100% | 5.96 | 100 | | | | | | | | |
| | 90% | 5.38 | 100 | 100 | | | | | | | |
| | 80% | 5.43 | 114 | 114 | 100 | | | | | | |
| | 70% | 4.71 | 113 | 113 | 99 | 100 | | | | | |
| | 60% | 4.48 | 125 | 125 | 110 | 111 | 100 | | | | |
| | 50% | 3.63 | 122 | 121 | 107 | 108 | 97 | 100 | | | |
| | 40% | 2.53 | 106 | 106 | 93 | 94 | 85 | 87 | 100 | | |
| | 30% | 2.06 | 116 | 115 | 101 | 102 | 92 | 95 | 109 | 100 | |
| | 20% | 1.61 | 135 | 134 | 118 | 119 | 108 | 111 | 127 | 117 | 100 |
| | 10% | 0.43 | 73 | 72 | 64 | 64 | 58 | 60 | 69 | 63 | 54 |
| C | 100% | 2.89 | 100 | | | | | | | | |
| | 90% | 2.22 | 86 | 100 | | | | | | | |
| | 80% | 2.50 | 108 | 126 | 100 | | | | | | |
| | 70% | 2.25 | 111 | 130 | 103 | 100 | | | | | |
| | 60% | 1.88 | 108 | 127 | 100 | 97 | 100 | | | | |
| | 50% | 1.86 | 129 | 151 | 119 | 116 | 119 | 100 | | | |
| | 40% | 1.11 | 96 | 112 | 89 | 86 | 89 | 80 | 100 | | |
| | 30% | 1.16 | 134 | 157 | 124 | 121 | 124 | 104 | 140 | 100 | |
| | 20% | 0.59 | 102 | 119 | 94 | 92 | 94 | 79 | 106 | 76 | 100 |
| | 10% | 0.05 | 17 | 20 | 16 | 16 | 16 | 13 | 18 | 13 | 17 |

As shown by table 1 starting with pure serum, the dilutions are incorrect (light gray). For each of the 3 samples, starting with serum diluted at 80%, good recoveries were obtained for dilutions of 10 at 10% (dark gray). Thus, wishing to reduce the number of samples, serums diluted at 50% i.e., at ½ will be used and these serums may still be diluted of 10 at 10% up to 20% i.e., ⅕ of the pure serum.

2) Precision intra and inter tests: the same sample (control serum or standard peptide) is measured 20 times on the same plate (intra-test) or the same sample (control serum or standard peptide) is measured on 10 different plates (inter-test) in order to check the variability of the values obtained (Table 2 and 3).

TABLE 2

Measurement precision of the peptide's range of sequence SEQ ID no. 1 intra and inter-test:

| | Intra-test | | Inter-test | |
|---|---|---|---|---|
| Peptide Range | Periostin peptide concentration (ng/ml) | Coefficient of variability (CV), % | Periostin peptide concentration (ng/ml) | CV, % |
| 1.33 | 1.362 ± 0.293 | 21.5 | 1.3 ± 0.25 | 19.1 |
| 2 | 2.15 ± 0.31 | 12.3 | 1.92 ± 0.25 | 12.9 |
| 4 | 3.965 ± 0.406 | 10.2 | 4.01 ± 0.52 | 13 |
| 10 | 10.045 ± 0.906 | 9 | 9.98 ± 0.7 | 7 |
| 40 | 40.607 ± 3.582 | 8.8 | 39.8 ± 2.48 | 6.2 |
| 100 | 98.197 ± 10.93 | 11.1 | 100.84 ± 8.24 | 8.2 |

TABLE 2-continued

Measurement precision of the peptide's range of sequence SEQ ID no. 1 intra and inter-test:

| | Intra-test | | Inter-test | |
|---|---|---|---|---|
| Peptide Range | Periostin peptide concentration (ng/ml) | Coefficient of variability (CV), % | Periostin peptide concentration (ng/ml) | CV, % |
| 400 | 425.426 ± 39.816 | 9.4 | 420.25 ± 37.75 | 9 |
| 1000 | 898.435 ± 77.993 | 8.7 | 901.65 ± 62.66 | 6.9 |

We observe the proper repeatability (CV<15%) of the peptide measurement used as a standard for determining the periostin concentration in serum samples by ELISA. Only the first range point (1.33 ng/ml) has less of as good repeatability since it is near the detection limit.

TABLE 3

Measurement precision of peptide minimally containing sequence SEQ ID no. 1 intra and inter-test in three serum samples

| Samples | Intra-test | | Inter-test | |
|---|---|---|---|---|
| | Periostin peptide concentration (ng/ml) | Coefficient of variability (CV), % | Periostin peptide concentration (ng/ml) | CV, % |
| A | 16.123 ± 1.160 | 7.2 | 16.53 ± 1.90 | 11.47 |
| B | 4.620 ± 0.560 | 12.1 | 4.83 ± 0.62 | 12.91 |
| C | 2.838 ± 0.329 | 11.6 | 2.96 ± 0.43 | 14.62 |

We observe the proper repeatability of the periostin measurement by the ELISA for serum samples with high, medium and low rates of periostin. Indeed, the CVs are below the established 15% limit, regardless of whether the sample is at the beginning, in the middle or the end of the range.

Example 3

Western Blot Analysis of the Specificity of the Antiserum Containing the Anti-Periostin Antibody This electrophoresis technique on polyacrylamide gel makes it possible to separate previously denatured proteins according to their molecular weight. Samples are taken up in a solution of Lithium Dodecyl Sulfate (NuPAGE®-LDS buffer) and reducer agent. They are then denatured at 70° C. for 10 minutes, then deposited on gel for migration of the proteins at 200V (180 mA) for 40 min.

The transfer of the proteins from the polyacrylamide gel on a membrane of PolyVinyliDene Fluoride (PVDF) is followed by a detection of the proteins immobilized by the antiserum specific to periostin. For the immunodetection, the membrane is placed in a saturation buffer TBS-Tween® surfactant 0.1%-Milk 3% for one hour at ambient temperature. The membrane is quickly washed in washing buffer then incubated with the antiserum diluted at 1/1000 for one hour at ambient temperature. After three 5-minute washes, the membrane is incubated for 1 hour at ambient temperature in the presence of the secondary anti-rabbit antibody diluted to 1/10000. The membrane is again rinsed 3 times for 5 minutes. The membrane is incubated for 1 minute in a chemiluminescent solution (ECL kit, Amersham). It is placed in contact with a photographic film for a variable time period (1-5 min) in an autoradiography cassette. The film is then revealed by incubation from a few seconds to one or two minutes in developing solvent then rinsed with water and fixed for one minute in fixing agent.

Figure 5:
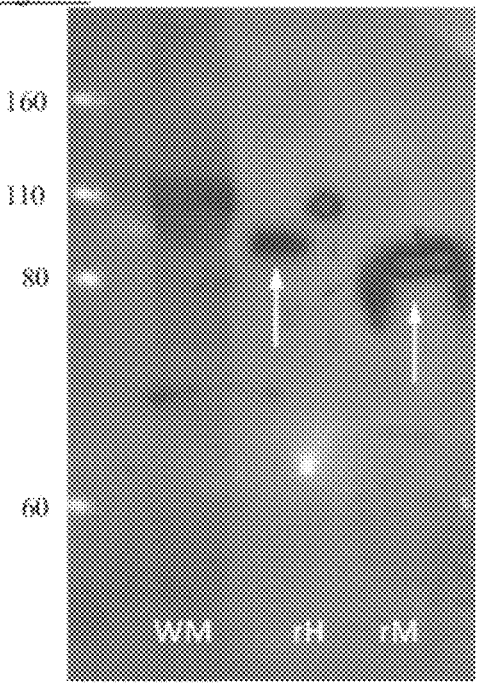
FIG. 5 represents a western blot analysis of the recognition of human and murine recombinant periostins by the specific antiserum of peptide sequence SEQ ID no. 1.

FIG. 5 corresponds to a photograph of a western blot on which murine and human recombinant periostins are used as control samples. A strip of each respective sample is observed between 80 and 110 kDa. With the periostin having a theoretical size of 90 kDa, we observe that the antiserum containing anti-periostin antibodies specific to the synthetic peptide sequence antigen minimally including a sequence of 6 to 30 amino acids minimally containing sequence SEQ ID no. 1, specifically recognizes the human and murine periostin.

Example 4

Determination of the Level of Periostin Serum in Breast Cancer Patients with Bone Metastases and Control Subjects Serum samples from 30 fasting breast cancer patients (department of medicine of the Institut Jules Bordet de Bruxelles) are analyzed. Before performing the doses, all serum samples had been preserved at −70° C. The breast cancer was confirmed by histological analysis for each of the patients. Among the 30 breast cancer patients, 15 have bone metastases visible in radiology. The patients had been under stable anti-tumor treatment for at least 4 weeks and had not received treatment for bisphosphonates for the previous 4 months. The patients had no history of other metabolic bone diseases. The rates of periostin serum were also measured in 18 healthy women and untreated (median age: 53, between the ages of 46 and 60) recruited from a blood donation program with no history of breast disease or metabolic bone disease. None of the control subjects had had treatment that could interfere with bone metabolism, including hormone replacement therapy in menopausal women.

The median age of the breast cancer patients with or without bone metastasis is respectively 58 and 66 years; they are positive to estrogen receptors respectively in 40% and 87% of the cases. Most of these patients show ductal-type mammary carcinomas (67%). For breast cancer patients with bone metastases, the type of bone metastases is evenly distributed among the lytic, blastic type and mixed with a metastatic load ≥5 in 67% of the cases.

Figure 6:
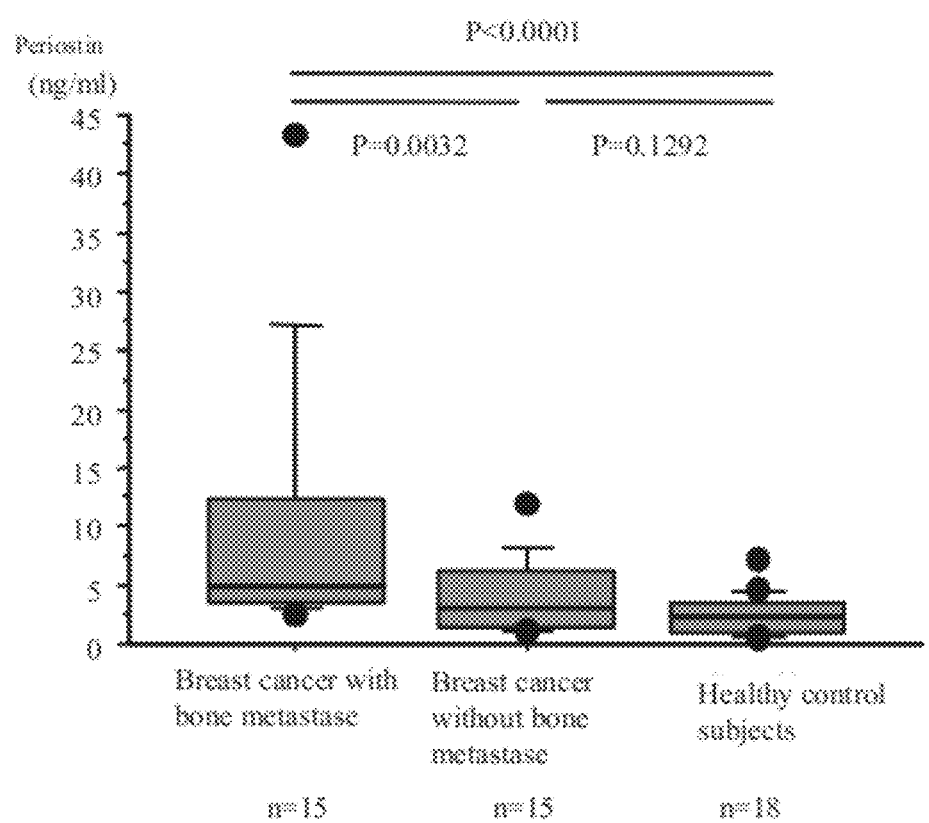
FIG. 6 is a graphic representation of periostin dosages using the antibody specific to detection sequence SEQ ID no. 1 according to the invention, in healthy individuals and individuals with breast cancer with or without bone metastases.

FIG. 6 corresponds to a chart illustrating results from a clinical study on healthy individuals and breast cancer individuals with or without bone metastasis, using the periostin marker via detection sequence SEQ ID no. 1 according to the invention. We observe that the average rate of periostin serum detected is significantly higher in individuals with metastasis (5.16±15.12 ng/ml) versus individuals with no bone metastasis (3.14±4.84 ng/ml) or healthy (2.37±2.56 ng/ml). This shows that the total periostin serum via detection sequence SEQ ID no. 1 according to the invention is a good indicator of the presence of breast cancer bone metastasis.

Example 5

Expression of Periostin in a Bone Metastasis Environment from Breast Cancer

The expression of periostin is evaluated by PCR and by ELISA with the antibody according to this invention directed against SEQ ID no. 1 in several human cell lines of breast and prostate cancer that metastase in the bone. The MDA-B02 cells of breast cancer are then injected in the artery of the tail of a mouse receiving zoledronic acid (biphosphonate) or a placebo. The expression of periostin is determined by quantitative immunohistochemistry (IHC) and PCR. The periostin serum and the traditional bone markers are also measured in the mice. The levels of periostin serum are measured in 30 breast cancer patients with bone metastases (n=15) or without bone metastases (n=15) and in 16 healthy patients.

None of the human cell lines cultivated in vitro expresses or secretes periostin. The murine—but not human—periostin is however markedly expressed in the micro bone environment of the mice that received an injection of MDA-B02 cells as opposed to the control mice. The stromal murine cells therefore secrete periostin in response to the presence of the injected human tumor cells. The immunohistochemistry shows that the periostin is located in the stromal cells of the bone marrow. As a result of the x-ray and traditional biochemical markers of the bone renewal, we observe that the zoledronic acid treatment markedly reduces bone lesions but it has a weak effect on the expression of the ARNm of periostin and the circulating rates. This shows that the expression of periostin is not linked to the bone remodeling in metastatic context. The periostin serum rates are significantly higher in breast cancer patients with bone metastases versus breast cancer patients without metastases (+64%, p=0.02) or in healthy patients (+117%, p=0.01).

Accordingly, bone metastases from breast cancer lead to the overexpression of periostin via stromal cells. Thus, periostin could be an early response biochemical marker of stromal cells to bone metastases from breast cancer. This would make it possible to detect the presence of bone metastases before the resorption of the bone and therefore before the possible detection by imaging and before the modification of bone remodeling markers, whence the earliness of possible diagnosis.

Example 6

Immunohistochemical Analysis of Mouse Bone Sections

Bones set in paraformaldehyde are decalcified with an Osteosoft solution (Merck, VWR, Val de Fontenay, France) before dehydration and inclusion in paraffin in accordance with the usual laboratory techniques. The immunohistochemistry was performed on 7-μm sections. Paraffin is briefly removed from the sections, endogenous peroxidases are blocked and the antigen is unmasked by incubation for 1 hour at ambient temperature in TRIS-Glycine buffer. Non specific sites are blocked for 1 hour at ambient temperature with TRIS buffer containing 5% of normal goat serum (NGS). The sections are then incubated over night at 4° C. with the primary antibody directed against sequence SEQ ID no. 1. As specificity control, the primary antibody is pre-incubated 1 hour at 37° C. with peptide from sequence SEQ ID no. 1 then placed in contact with the sections over night at 4° C. After washing, following incubation at ambient temperature for 1 hour with an anti IgG rabbit antibody coupled with horseradish peroxidase (Rabbit IgG HRP-linked Whole Ab; Source: Donkey; GE Healthcare). Lastly, the peroxidase is placed in the presence of DAB (diaminobenzidine) that gives a brown marking to the immunoreagent sites. A counter coloring is performed with Mayers hematoxyline that colors the cell cores blue.

Figure 7:
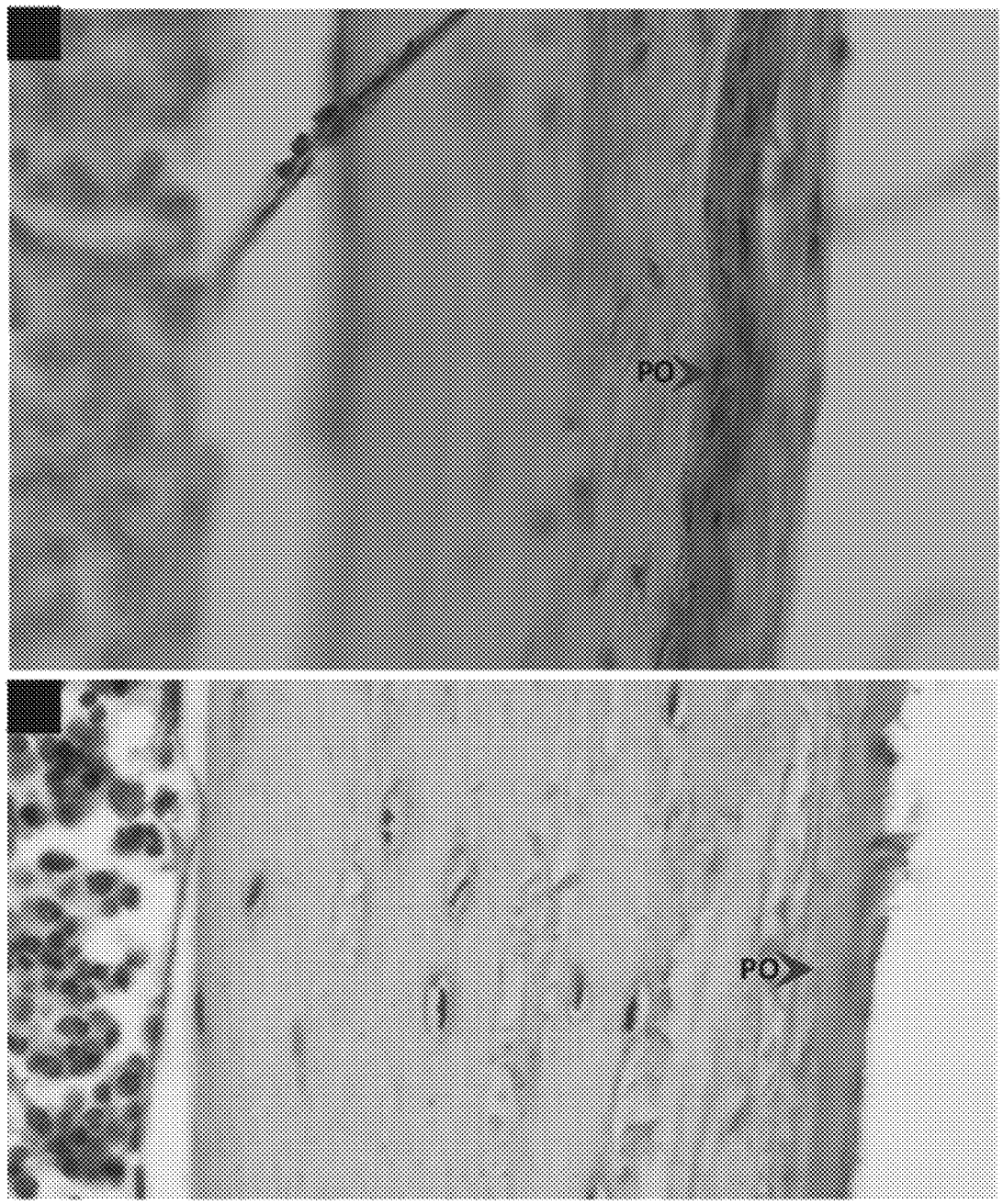
FIG. 7 shows an immunohistochemical analysis of a section of mouse tibia bone tissue during growth (FIG. 7A) and adult (FIG. 7B) marked with the specific antiserum of peptide sequence SEQ ID no. 1.

FIG. 7 shows an immunohistochemical analysis conducted with the antibody specific to SEQ ID no. I of cuts of bone tissue. When bone sections of growing mice are incubated in the presence of the specific antiserum, a coloring appears near the periostea (cf. FIG. 7A). During growth, periosteum apposition activity (that permits the radial growth of the bone by "intramembrane ossification") is reduced. Our analysis shows that the periosteum of adult mice is finer and not marked by the antibody specific to SEQ ID no. 1 (cf. FIG. 7B). This suggests that SEQ ID no. 1 is an intermembrane ossification and periosteum apposition marker.

The invention claimed is:

1. An isolated anti-periostin antibody, or one of its functional fragments, said antibody or its functional fragments able to recognize only an epitope comprised in the peptide consisting of SEQ ID No. 1, SEQ ID No. 2, or SEQ ID No. 3, wherein said functional fragments are selected from the group consisting of fragment Fv, fragment Fab that contains a site of recognition specific to the antigen, and fragment F(ab')$_2$ that contains at least two recognition sites specific to the antigen.

2. Periostin detection kit, in a biological sample, comprising an anti-periostin antibody of, reagents and equipment for the detection, and optionally for the dosage, of anti-periostin antibody/periostin complexes, and use instructions wherein said periostin antibody is an isolated anti-periostin antibody, or one of its functional fragments, said antibody or its functional fragments able to recognize only an epitope comprised in the peptide consisting of SEQ ID No. 1, SEQ ID No. 2, or SEQ ID No. 3, wherein said functional fragments are selected from the group consisting of fragment Fv, fragment Fab that contains a site of recognition specific to the antigen, and fragment F(ab')$_2$ that contains at least two recognition sites specific to the antigen.

3. Undercarboxylated periostin (UCP) detection and dosage kit which includes an anti-periostin antibody of, reagents and equipment for the isolation, and optionally for the dosage, of anti-periostin antibody/periostin complexes, a support having more affinity for carboxylated periostin (CP) than UCP, or, conversely, a support having more affinity for UCP than CP, and use instructions wherein said periostin antibody is an isolated anti-periostin antibody, or one of its functional fragments, said antibody or its functional fragments able to recognize only an epitope comprised in the peptide consisting of SEQ ID No.1, SEQ ID No.2, or SEQ ID No.3, wherein said functional fragments are selected from the group consisting of fragment Fv, fragment Fab that contains a site of recognition specific to the antigen, and fragment F(ab')$_2$ that contains at least two recognition sites specific to the antigen.

4. The kit according to claim 3, wherein said support is a support having an affinity to CP greater than that vis-à-vis the UCP.

5. The kit according to claim 4, wherein said support includes hydroxyapatite.

6. The kit according to claim 4, wherein said support includes bone mineral matrix including hydroxyapatite in the form of crystals.

* * * * *

SEQUENCE LISTING

```
<160> NUMBER OF SEQ ID NOS: 5

<210> SEQ ID NO 1
<211> LENGTH: 18
<212> TYPE: PRT
<213> ORGANISM: homo sapiens

<400> SEQUENCE: 1

Lys Gly Phe Glu Pro Gly Val Thr Asn Ile Leu Lys Thr Thr Gln Gly
1               5                   10                  15

Ser Lys

<210> SEQ ID NO 2
<211> LENGTH: 17
<212> TYPE: PRT
<213> ORGANISM: homo sapiens

<400> SEQUENCE: 2

Glu Thr Leu Glu Gly Asn Thr Ile Glu Ile Gly Cys Asp Gly Asp Ser
1               5                   10                  15

Ile

<210> SEQ ID NO 3
<211> LENGTH: 17
<212> TYPE: PRT
<213> ORGANISM: mus musculus

<400> SEQUENCE: 3
```

```
Glu Ala Ile Thr Gly Gly Ala Val Gly Glu Ala Ile Thr Gly Gly Ala
1               5                   10                  15

Val
```

<210> SEQ ID NO 4
<211> LENGTH: 836
<212> TYPE: PRT
<213> ORGANISM: homo sapiens

<400> SEQUENCE: 4

```
Met Ile Pro Phe Leu Pro Met Phe Ser Leu Leu Leu Leu Ile Val
1               5                   10                  15

Asn Pro Ile Asn Ala Asn Asn His Tyr Asp Lys Ile Leu Ala His Ser
                20                  25                  30

Arg Ile Arg Gly Arg Asp Gln Gly Pro Asn Val Cys Ala Leu Gln Gln
            35                  40                  45

Ile Leu Gly Thr Lys Lys Lys Tyr Phe Ser Cys Lys Asn Trp Tyr
        50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
                100                 105                 110

Thr Gln Arg Tyr Ser Asp Ala Ser Lys Leu Arg Glu Glu Ile Glu Gly
            115                 120                 125

Lys Gly Ser Phe Thr Tyr Phe Ala Pro Ser Asn Glu Ala Trp Asp Asn
        130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
                180                 185                 190

Gly Leu Phe Ile Asn His Tyr Pro Asn Gly Val Val Thr Val Asn Cys
            195                 200                 205

Ala Arg Ile Ile His Gly Asn Gln Ile Ala Thr Asn Gly Val Val His
        210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Phe Met Gly Asp Lys Val Ala Ser Glu Ala Leu Met Lys Tyr His
        290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350
```

-continued

```
Thr Asn Asn Gly Val Ile His Leu Ile Asp Gln Val Leu Ile Pro Asp
            355                 360                 365

Ser Ala Lys Gln Val Ile Glu Leu Ala Gly Lys Gln Gln Thr Thr Phe
        370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Val Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
    450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
    530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
    610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Thr Thr Lys
            660                 665                 670

Ile Ile Thr Lys Val Val Glu Pro Lys Ile Lys Val Ile Glu Gly Ser
        675                 680                 685

Leu Gln Pro Ile Ile Lys Thr Glu Gly Pro Thr Leu Thr Lys Val Lys
    690                 695                 700

Ile Glu Gly Glu Pro Glu Phe Arg Leu Ile Lys Gly Glu Thr Ile
705                 710                 715                 720

Thr Glu Val Ile His Gly Glu Pro Ile Ile Lys Lys Tyr Thr Lys Ile
                725                 730                 735

Ile Asp Gly Val Pro Val Glu Ile Thr Glu Lys Glu Thr Arg Glu Glu
            740                 745                 750

Arg Ile Ile Thr Gly Pro Glu Ile Lys Tyr Thr Arg Ile Ser Thr Gly
        755                 760                 765
```

-continued

```
Gly Gly Glu Thr Glu Thr Leu Lys Lys Leu Leu Gln Glu Val
    770             775             780

Thr Lys Val Thr Lys Phe Ile Glu Gly Asp Gly His Leu Phe Glu
785             790             795             800

Asp Glu Glu Ile Lys Arg Leu Leu Gln Gly Asp Thr Pro Val Arg Lys
                805             810             815

Leu Gln Ala Asn Lys Lys Val Gln Gly Ser Arg Arg Leu Arg Glu
            820             825             830

Gly Arg Ser Gln
        835

<210> SEQ ID NO 5
<211> LENGTH: 838
<212> TYPE: PRT
<213> ORGANISM: mus musculus

<400> SEQUENCE: 5

Met Val Pro Leu Leu Pro Leu Tyr Ala Leu Leu Leu Phe Leu Cys
1               5               10              15

Asp Ile Asn Pro Ala Asn Ala Asn Ser Tyr Tyr Asp Lys Val Leu Ala
                20              25              30

His Ser Arg Ile Arg Gly Arg Asp Gln Gly Pro Asn Val Cys Ala Leu
            35              40              45

Gln Gln Ile Leu Gly Thr Lys Lys Tyr Phe Ser Ser Cys Lys Asn
    50              55              60

Trp Tyr Gln Gly Ala Ile Cys Gly Lys Lys Thr Thr Val Leu Tyr Glu
65              70              75              80

Cys Cys Pro Gly Tyr Met Arg Met Glu Gly Met Lys Gly Cys Pro Ala
                85              90              95

Val Met Pro Ile Asp His Val Tyr Gly Thr Leu Gly Ile Val Gly Ala
            100             105             110

Thr Thr Thr Gln His Tyr Ser Asp Val Ser Lys Leu Arg Glu Glu Ile
        115             120             125

Glu Gly Lys Gly Ser Tyr Thr Tyr Phe Ala Pro Ser Asn Glu Ala Trp
130             135             140

Glu Asn Leu Asp Ser Asp Ile Arg Arg Gly Leu Glu Asn Asn Val Asn
145             150             155             160

Val Glu Leu Leu Asn Ala Leu His Ser His Met Val Asn Lys Arg Met
                165             170             175

Leu Thr Lys Asp Leu Lys His Gly Met Val Ile Pro Ser Met Tyr Asn
            180             185             190

Asn Leu Gly Leu Phe Ile Asn His Tyr Pro Asn Gly Val Val Thr Val
        195             200             205

Asn Cys Ala Arg Val Ile His Gly Asn Gln Ile Ala Thr Asn Gly Val
    210             215             220

Val His Val Ile Asp Arg Val Leu Thr Gln Ile Gly Thr Ser Ile Gln
225             230             235             240

Asp Phe Leu Glu Ala Glu Asp Leu Ser Ser Phe Arg Ala Ala Ala
                245             250             255

Ile Thr Ser Asp Leu Leu Glu Ser Leu Gly Arg Asp Gly His Phe Thr
            260             265             270

Leu Phe Ala Pro Thr Asn Glu Ala Phe Glu Lys Leu Pro Arg Gly Val
        275             280             285

Leu Glu Arg Ile Met Gly Asp Lys Val Ala Ser Glu Ala Leu Met Lys
    290             295             300
```

```
Tyr His Ile Leu Asn Thr Leu Gln Cys Ser Glu Ala Ile Thr Gly Gly
305                 310                 315                 320

Ala Val Phe Glu Thr Met Glu Gly Asn Thr Ile Glu Ile Gly Cys Glu
            325                 330                 335

Gly Asp Ser Ile Ser Ile Asn Gly Ile Lys Met Val Asn Lys Lys Asp
        340                 345                 350

Ile Val Thr Lys Asn Gly Val Ile His Leu Ile Asp Glu Val Leu Ile
                355                 360                 365

Pro Asp Ser Ala Lys Gln Val Ile Glu Leu Ala Gly Lys Gln Gln Thr
        370                 375                 380

Thr Phe Thr Asp Leu Val Ala Gln Leu Gly Leu Ala Ser Ser Leu Lys
385                 390                 395                 400

Pro Asp Gly Glu Tyr Thr Leu Leu Ala Pro Val Asn Asn Ala Phe Ser
            405                 410                 415

Asp Asp Thr Leu Ser Met Asp Gln Arg Leu Leu Lys Leu Ile Leu Gln
        420                 425                 430

Asn His Ile Leu Lys Val Lys Val Gly Leu Ser Asp Leu Tyr Asn Gly
            435                 440                 445

Gln Ile Leu Glu Thr Ile Gly Gly Lys Gln Leu Arg Val Phe Val Tyr
450                 455                 460

Arg Thr Ala Ile Cys Ile Glu Asn Ser Cys Met Val Arg Gly Ser Lys
465                 470                 475                 480

Gln Gly Arg Asn Gly Ala Ile His Ile Phe Arg Glu Ile Ile Gln Pro
            485                 490                 495

Ala Glu Lys Ser Leu His Asp Lys Leu Arg Gln Asp Lys Arg Phe Ser
            500                 505                 510

Ile Phe Leu Ser Leu Leu Glu Ala Ala Asp Leu Lys Asp Leu Leu Thr
        515                 520                 525

Gln Pro Gly Asp Trp Thr Leu Phe Ala Pro Thr Asn Asp Ala Phe Lys
        530                 535                 540

Gly Met Thr Ser Glu Glu Arg Glu Leu Leu Ile Gly Asp Lys Asn Ala
545                 550                 555                 560

Leu Gln Asn Ile Ile Leu Tyr His Leu Thr Pro Gly Val Tyr Ile Gly
                565                 570                 575

Lys Gly Phe Glu Pro Gly Val Thr Asn Ile Leu Lys Thr Thr Gln Gly
            580                 585                 590

Ser Lys Ile Tyr Leu Lys Gly Val Asn Glu Thr Leu Leu Val Asn Glu
        595                 600                 605

Leu Lys Ser Lys Glu Ser Asp Ile Met Thr Thr Asn Gly Val Ile His
        610                 615                 620

Val Val Asp Lys Leu Leu Tyr Pro Ala Asp Ile Pro Val Gly Asn Asp
625                 630                 635                 640

Gln Leu Leu Glu Leu Leu Asn Lys Leu Ile Lys Tyr Ile Gln Ile Lys
            645                 650                 655

Phe Val Arg Gly Ser Thr Phe Lys Glu Ile Pro Met Thr Val Tyr Thr
            660                 665                 670

Thr Lys Ile Ile Thr Lys Val Val Glu Pro Lys Ile Lys Val Ile Gln
        675                 680                 685

Gly Ser Leu Gln Pro Ile Ile Lys Thr Glu Gly Pro Ala Met Thr Lys
        690                 695                 700

Ile Gln Ile Glu Gly Asp Pro Asp Phe Arg Leu Ile Lys Glu Gly Glu
705                 710                 715                 720
```

```
Thr Val Thr Glu Val Ile His Gly Glu Pro Val Ile Lys Lys Tyr Thr
            725                 730                 735

Lys Ile Ile Asp Gly Val Pro Val Glu Ile Thr Glu Lys Gln Thr Arg
            740             745                 750

Glu Glu Arg Ile Ile Thr Gly Pro Glu Ile Lys Tyr Thr Arg Ile Ser
        755             760                 765

Thr Gly Gly Gly Glu Thr Gly Glu Thr Leu Gln Lys Phe Leu Gln Lys
    770             775             780

Glu Val Ser Lys Val Thr Lys Phe Ile Glu Gly Gly Asp Gly His Leu
785             790             795             800

Phe Glu Asp Glu Glu Ile Lys Arg Leu Leu Gln Gly Asp Thr Pro Ala
            805             810             815

Lys Lys Ile Pro Ala Asn Lys Arg Val Gln Gly Pro Arg Arg Arg Ser
            820             825             830

Arg Glu Gly Arg Ser Gln
        835
```